US008481287B2

(12) United States Patent
Perille Collins

(10) Patent No.: US 8,481,287 B2
(45) Date of Patent: Jul. 9, 2013

(54) METHOD, VECTOR AND SYSTEM FOR EXPRESSING POLYPEPTIDES

(75) Inventor: Mary Lynne Perille Collins, Milwaukee, WI (US)

(73) Assignee: The UWM Research Foundation, Inc., Milwaukee, WI (US)

( * ) Notice: Subject to any disclaimer, the term of this patent is extended or adjusted under 35 U.S.C. 154(b) by 162 days.

(21) Appl. No.: 12/812,300

(22) PCT Filed: Jan. 9, 2009

(86) PCT No.: PCT/US2009/030564
§ 371 (c)(1),
(2), (4) Date: Jul. 9, 2010

(87) PCT Pub. No.: WO2009/089424
PCT Pub. Date: Jul. 16, 2009

(65) Prior Publication Data
US 2010/0285528 A1    Nov. 11, 2010

Related U.S. Application Data

(60) Provisional application No. 61/020,095, filed on Jan. 9, 2008.

(51) Int. Cl.
*C12N 15/09* (2006.01)
*C12N 1/00* (2006.01)
*C12N 1/21* (2006.01)

(52) U.S. Cl.
USPC ................ 435/69.1; 435/243; 435/252.3

(58) Field of Classification Search
None
See application file for complete search history.

(56) References Cited

U.S. PATENT DOCUMENTS

| 6,465,216 | B2 | 10/2002 | Laible et al. |
| 6,680,179 | B1 | 1/2004 | Perille-Collins et al. |
| 6,951,741 | B2 | 10/2005 | Mary Lynne et al. |
| 2004/0086969 | A1 | 5/2004 | Mary Lynne et al. |
| 2007/0092943 | A1 | 4/2007 | Laible et al. |

OTHER PUBLICATIONS

Kimble et al., Curr. PRotocols in Protein Science, May 2004, 9,9,1-9,9,19.*
Schultz et al., J. Bacter. 149(1): 181-190, 1982.*
Arechaga, I. et al., "Characterisation of new intracellular membranes in *Escherichia coli* accompanying large scale over-production of the b subunit of F1F-ATP synthase," FEBS Lett. (2000) 482:215-219.
Benson, J.A., "Production and assembly of light-harvesting antenna in *Rhodospirillum rubrum*," M.S. Thesis, University of Wisconsin-Milwaukee (2007) 65 pages.
Brantner, C.A. et al., "Intracellular localization of the particulate methane monooxygenase and methanol dehydrogenase in methylomicrobium album BG8," Arch. Microbiol. (2002) 178:59-64.

Butzin, N.C. et al., "A new system for heterologous expression of membrane proteins: *Rhodospirillum rubrum*," Prot. Exp. Purif. (2010) 70:88-94.
Butzin, N.C. et al., "Role of the PufB and PufA c-terminal extensions in the assembly of *Rhodospirillum rubrum* light-harvesting antenna," Curr. Microbiol. (2010) 60:301-306.
Butzin, N.C., "Development of methodology to identify promoters and use sacB selection to construct knockout mutants in *Rhodospirillum rubrum*," M.S. Thesis, University of Wisconsin-Milwaukee (2005) 21-24, 28-29, 36-45.
Cheng, Y.S. et al., "Role of the H protein in assembly of the photochemical reaction center and intracytoplasmic membrane in *Rhodospirillum rubrum*," J. Bacteriol. (2000) 182(5):1200-1207.
Collins, M.L.P. et al., "Effect of copper on methylomonas albus BG8," Appl. Environ. Microb. (1991) 57(4):1261-1264.
Crook, S.M. et al., "Immunocytochemical ultrastructural analysis of chromatophore membrane formation in *Rhodospirillum rubrum*," J. Bact. (1986) 167(1):89-95.
Dehio, C. et al., "Maintenance of broad-host-range incompatibility group P and group Q plasmids and transpotiion of Tn5 in *Bartonella henselae* following conjugal plasmid transfer from *Escherichia coli*," J. Bacteriol. (1997) 179:538-540.
Feissner, R. et al., "Chemiluminescent-based methods to detect subpicomole levels of C-type cytochromes," Anal. Biochem. (2003) 315:90-94.
Hessner, M.J. et al., "Construction, characterization, and complementation of *Rhodospirillum rubrum* puf region mutants," J. Bacteriol. (1991) 173(18):5712-5722.
Holt, S.C. et al., "Location of chlorophyl in *Rhodospirillum rubrum*," J. Bacter. (1965) 89(5):1402-1412.
Hu, Z. et al., "A powerful hybrid puc operon promoter tightly regulated by both IPTG and low oxygen level," Biochemistry (Moscow) (2010) 75(4):519-525.
Kovach, M.E. et al., "Four new derivatives of the broad-host-range cloning vector pBBR1MCS, carrying different antibiotic-resistance cassettes," Gene (1995) 166:175-176.
LeBlanc, H.N. et al., "*Rhodobacter capsulatus* puc operon: promoter location, transcript sizes and effects of deletions on photosynthetic growth," J. Gen. Microbiol. (1993) 139:101-109.
Lefman, J. et al., "Three-dimensional electron microscopic imaging of membrane invaginantions in *Escherichia coli* overproducing the chemotaxis receptor Tsr," J. Bacteriol. (2004) 186(15):5052-5061.
Masuda, S. et al., "Null mutation of HvrA compensates for loss of an essential relA/spoT-like gene in *Rhodobacter capsulatus*," J. Bacteriol. (2004) 186(1):235-239.
Mueller, P.R. et al., "Identification of two distinct loctate dehydrogenases in *Rhodospirillum rubrum*," J. Bacter. (1983) 153(3):1562-1566.
Myers, C.R. et al., "Cell-cycle-specific fluctuation in cytoplasmic membrane composition in aerobically grown *Rhodospirillum rubrum*," J. Bacteriol. (1987) 169(12):5445-5451.

(Continued)

*Primary Examiner* — Nancy T Vogel
(74) *Attorney, Agent, or Firm* — Michael Best & Friedrich LLP

(57) ABSTRACT

Disclosed herein are methods and systems for expressing a polypeptide in a *Rhodospirillum* species. The methods include introducing an expression vector having a nucleic acid sequence encoding the polypeptide operably linked to a puc promoter into the *Rhodospirillum* bacterium and growing the *Rhodospirillum* bacterium under conditions that allow expression of the polypeptide. Vectors for expressing a membrane polypeptide in a *Rhodospirillum* species are disclosed. The vectors include a puc promoter and a nucleic acid encoding a membrane polypeptide.

30 Claims, 5 Drawing Sheets

OTHER PUBLICATIONS

Myers, C.R. et al., "Cell-cycle-specific oscillation in the composition of chromatophore membrane in *Rhodospirillum rubrum*," J. Bacteriol. (1986) 166(3):818-823.

Nickens, D.G. et al., "Analysis of the puc operon promoter from *Rhodobacter capsulatus*," J. Bacteriol. (1998) 180(16):4270-4277.

Nieboer, M. et al., "The alkane oxidation system of *Pseudomonas oleovorans*: induction of the alk genes in *Escherichia coli* W3110 (pGEc47) affects membrane biogenesis and results in overexpression of alkane hydroylase in a distinct cytoplasmic membrane subfraction," Mol. Microbiol. (1993) 8(6):1039-1051.

Omerod, J.G. et al., "Light-dependent utilization of organic compounds and photoproduction of molecular hydrogen by photosynthetic bacteria; relationships with nitrogen metabolism," Arch. Biochem. Biophys. (1961) 94:449-463.

Roy, A. et al., "Employing *Rhodobacter sphaeroides* to functionally express and purify human G protein-coupled receptors," Biol. Chem. (2008) 389:69-78.

Weiner, J.H. et al., "Overproduction of fumarate reductase in *Escherichia coli* induces a novel intracellular lipid-protein organelle," J. Bacter. (1984) 158(2):590-596.

Yano, T. et al., "SacB-5-fluoroorotic acid-pyrE-based bidirectional selection for integration of unmarked alleles into the chromosome of *Rhodobacter capsulatus*," Appl. Environ. Microbiol. (2005) 71(6):3014-3024.

International Search Report and Written Opinion for Application No. PCT/US2009/030564 dated Mar. 27, 2009 (9 pages).

Butzin, N.C., "Production of heterologous membrane proteins in *Rhodospirillum rubrum*," Ph.D. Thesis, University of Wisconsin-Milwaukee (2009) (95 pgs).

J. Berard, et al., "Mapping of the puh Messenger RNAs from *Rhodospirillum rubrum*," J. Biol. Chem. 264 (18):10897-10903, 1989 (7 pgs).

J. Berard and G. Gingras, "The puh Structural Gene Coding for the H Subunit of the *Rhodospirillum rubrum* Photoreaction Center," Biochem. Cell. Biol. 69:122-131, 1991 (10 pgs).

J.M. Blatny, et al., "Construction and Use of a Versatile Set of Broad-Host-Range Cloning and Expression Vectors Based on the RK2 Replicon," Appl. Env. Microbiol. 63(2):370-379, 1997 (11 pgs).

Y.S. Cheng, "Molecular Analysis of Bacterial Intracytoplasmic Membrane Proteins," pp. 1-97, 1998 (Thesis) (112 pgs).

B.C. Jester, "Construction and Characterization of a puf Null Mutant of *Rhodospirillum rubrum*," pp. 1-45, 1998 (Thesis) (52 pgs).

N.T. Keen, et al., "Improved Broad-Host-Range Plasmids for DNA Cloning in Gram-negative Bacteria," Gene 70:191-197, 1988 (7 pgs).

W.R. Jones, et al., "Mutants of *Rhodobacter sphaeroides* Lacking One or More Pigment-Protein Complexes and Complementation with Reaction-Centre, LH1, and LH2 Genes," Molec. Microbiol 6(9):1173-1184, 1992 (13 pgs).

I.Y. Lee and M.L.P. Collins, "Identification and Partial Sequence of the BchA Gene of *Rhodospirillum rubrum*," Curr. Microbiol. 27:85-90, 1993 (6 pgs).

Grunwald et al. J. Bacteriol. 1995, vol. 177, No. 3, pp. 628-635 (9 pgs).

\* cited by examiner

METHOD, VECTOR AND SYSTEM FOR EXPRESSING POLYPEPTIDES

CROSS-REFERENCE TO RELATED APPLICATIONS

This patent application is a national stage filing under 35 U.S.C. 371 of International Application No. PCT/US2009/030564, filed 9 Jan. 2009, which claims the benefit of priority to U.S. Patent Application No. 61/020,095, filed 9 Jan. 2008, the disclosures of which are incorporated by reference herein in their entireties. Priority to each application is hereby claimed.

STATEMENT REGARDING FEDERALLY SPONSORED RESEARCH

This invention was made with government support under grant number R21 GM57322 awarded by the National Institutes of Health. The government has certain rights in the invention.

BACKGROUND

Membrane proteins are extremely important for normal cellular functions. For example, membrane proteins are the means by which cells communicate, transduce signals and transport metabolites. Membrane proteins have proven much more difficult to study than soluble proteins at least in part due to their relatively hydrophobic membrane spanning region. Membrane proteins are often expressed at low levels natively and many can not be isolated in an active form in the absence of membranes. Using traditional protein expression systems, it has been difficult to achieve expression of heterologous membrane proteins because these proteins are often unstable when not localized to the membrane. Heterologously expressed membrane protein are insoluble and thus cause formation of inclusion bodies or even cell death. The ability to generate the quantities of membrane proteins necessary for experimentation has been hampered. In addition, even in systems affording adequate expression of membrane proteins, purification or isolation of these proteins has proven difficult.

Therefore, there is a need in the art for methods of expressing polypeptides, particularly membrane polypeptides, in the context of a membrane such that these proteins can be studied in a form that approximates their native environment. There is also a need for methods of isolating or purifying the expressed polypeptides in functional form.

SUMMARY OF THE INVENTION

In one aspect, the present invention provides a strain of biological material designated *Rhodospirillum rubrum* H2 and deposited under the terms of the Budapest Treaty and in accordance with 37 C.F.R. §§1.801-1.809 on May 9, 2013 with the American Type Culture Collection (ATCC), Manassas, Va, under Accession Number PTA-120349.

A method of expressing a polypeptide in a *Rhodospirillum* species is disclosed. The *Rhodospirillum* species includes a nucleic acid sequence encoding the polypeptide operably linked to a puc promoter selected from the group consisting of SEQ ID NO: 1, a fragment of SEQ ID NO: 1, and SEQ ID NO:2. The *Rhodospirillum* species is grown under conditions that allow expression of the polypeptide.

In another aspect, a method of producing a *Rhodospirillum* species capable of expressing a polypeptide is provided. The method includes introducing an expression vector comprising a nucleic acid sequence encoding the polypeptide operably linked to a puc promoter selected from the group consisting of SEQ ID NO: 1, a fragment of SEQ ID NO: 1, and SEQ ID NO:2 into the *Rhodospirillum* species.

In yet another aspect, a vector for expressing a membrane polypeptide in a *Rhodospirillum* species is provided. The vector includes a puc promoter selected from the group consisting of SEQ ID NO: 1, a fragment of SEQ ID NO: 1, and SEQ ID NO:2, and a nucleic acid encoding a membrane polypeptide. The nucleic acid is operably connected to the puc promoter to allow expression of the membrane polypeptide. A *Rhodospirillum* including the vector is also provided.

In a further aspect, a system for expressing a polypeptide in a *Rhodospirillum* species is disclosed. The system includes the *Rhodospirillum* and a cloning vector comprising a puc promoter selected from the group consisting of SEQ ID NO: 1, a fragment of SEQ ID NO: 1, and SEQ ID NO:2.

DETAILED DESCRIPTION

Figure 1:
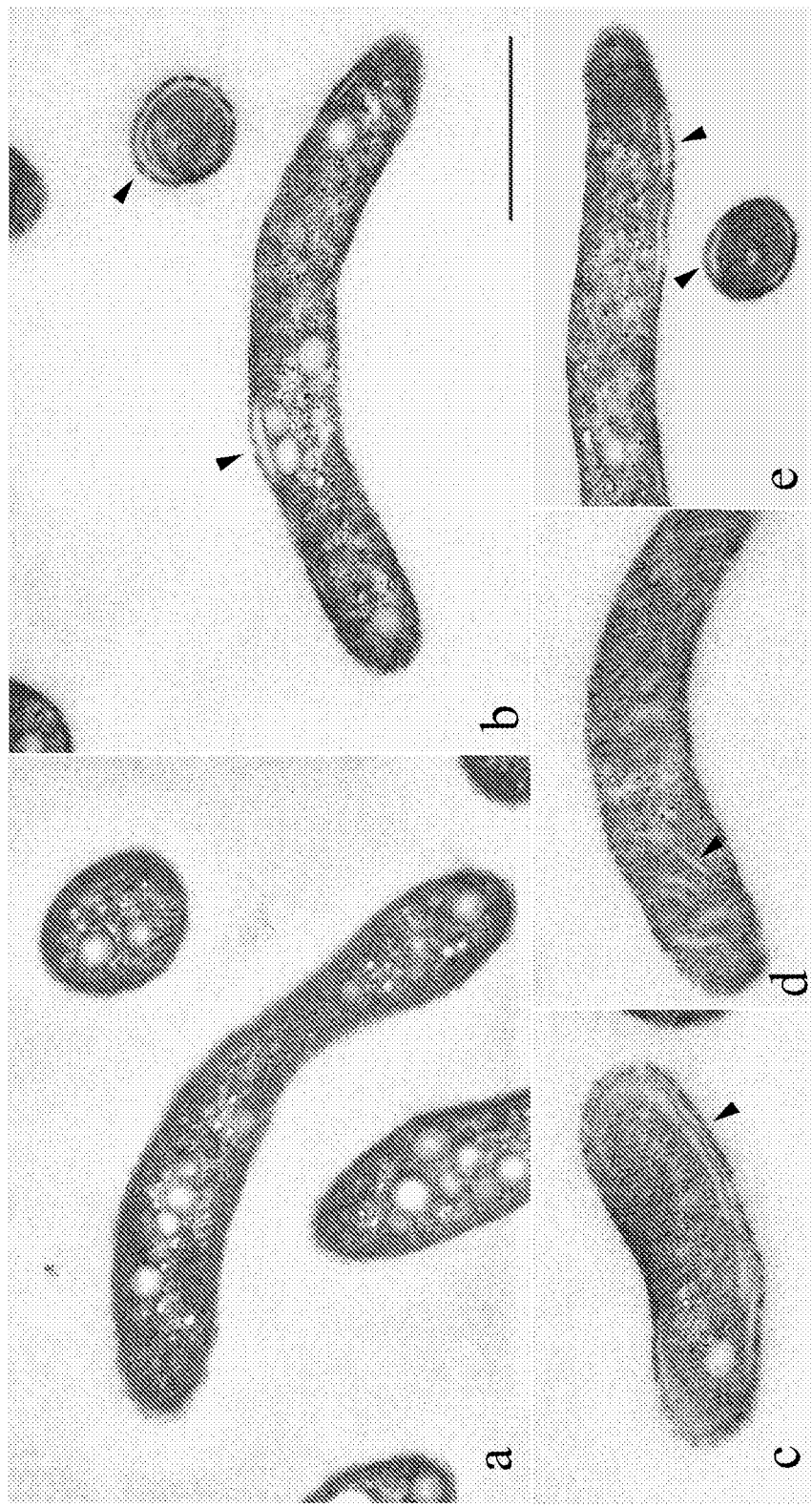
FIG. 1 is a set of electron micrographs of ultrathin sections of *R. rubrum* strains incubated under semi-aerobic conditions showing that (a) H2 with pUCTerm (vector control) does not form intracytoplasmic membrane (ICM) but (b-e) H2 with pPUCMscL (expressing MscL) does form ICM. Arrowheads indicate ICM. The bar is 1 μm.

Methods, systems and vectors for expressing polypeptides are provided herein. The methods, systems and vectors take advantage of the ability of *Rhodospirillum* species to form an intracytoplasmic membrane (ICM). *Rhodospirillum* are facultative phototrophic purple non-sulfur bacteria which are capable of growing phototrophically under anaerobic light conditions or by respiration under aerobic or anaerobic conditions in the dark. The *Rhodospirillum* photosynthetic apparatus is localized to the ICM. Non-native membrane proteins can be expressed by the *Rhodospirillum* and will localize to the ICM. Because *Rhodospirillum* are capable of growth under conditions for which the photosynthetic apparatus is not required, mutants of *Rhodospirillum* in which the photosynthetic apparatus has been disrupted are viable.

Under reduced oxygen concentration, the photosynthetic apparatus is induced and *Rhodospirillum* forms an ICM where the photosynthetic apparatus is located. This apparatus consists of the light-harvesting antenna (LH) and the photochemical reaction center (RC). The pigment-binding proteins, LH-α, LH-β, RC-L and RC-M, are encoded by the puf operon, while RC-H is encoded by puhA. Disrupting or reducing expression of the native *Rhodospirillum* ICM proteins allows for increased expression and incorporation of non-native membrane proteins in the ICM. In addition, the ICM and its associated proteins can be isolated by differential centrifugation.

Methods of expressing a polypeptide in a *Rhodospirillum* species by introducing an expression vector that includes a nucleic acid sequence encoding the polypeptide operably linked to a *Rhodobacter capsulatus* puc promoter and then growing the *Rhodospirillum* under conditions that allow expression of the polypeptide are provided. In another aspect, methods of producing a *Rhodospirillum* species capable of expressing a polypeptide by introducing an expression vector that contains a nucleic acid sequence encoding the polypeptide operably linked to a puc promoter into the *Rhodospirillum* species are provided. In another aspect, *Rhodospirillum* species containing a vector with the puc promoter operably connected to a nucleic acid encoding a polypeptide are provided.

The *Rhodobacter capsulatus* puc promoter was previously characterized. See Nickens and Bauer, J. Bacteriol. (1998) 180 (16): 4270-4277. The puc promoter includes SEQ ID NO:1 and fragments of SEQ ID NO:1 having promoter activity, including, for example, SEQ ID NO:2. Fragments of SEQ ID NO: 1 having promoter activity are capable of inducing expression of nucleic acids that are operably linked to the fragment. For example, SEQ ID NO: 2 is a fragment of SEQ ID NO:1 and, as shown in the Examples, SEQ ID NO: 2 is capable of inducing expression of an operably linked nucleic acid. Those of skill in the art will appreciate that fragments of SEQ ID NO: 1 containing the 3' portion of the sequence, particularly those which encompass SEQ ID NO: 2, are likely to be active promoters capable of inducing expression of operably linked nucleic acids. One of skill in the art could evaluate the ability of a fragment of SEQ ID NO: 1 to induce expression using any suitable method, including those described in the Examples below.

The puc promoter drives expression of several genes thought to be involved in the photosynthetic apparatus of *Rhodobacter capsulatus*. The puc promoter is induced by low light and reduced oxygen tension in *Rhodobacter*. As demonstrated in the Examples, the puc promoter is operable in *Rhodospirillum* rubrum and is capable of driving the expression of a heterologous polypeptide that localizes to the ICM. The puc promoter is also induced in *Rhodospirillum* when the bacteria are grown under semi-aerobic conditions, similar to what would be expected in *Rhodobacter*. The puc genes do not have homologs in *Rhodospirillum*, so it was surprising that the promoter functioned well in this background. Indeed, of the promoters tested to date (i.e., puc, puhA, puf and cbb), the puc promoter seems to be the strongest promoter for expression of polypeptides in *Rhodospirillum* on the basis of signal strength of the expressed proteins in western blots. Previous reports demonstrated that *R. rubrum* can be genetically engineered to express non-native membrane proteins in the ICM by disrupting production of one or more of the proteins natively associated with the ICM and using the native puf and puh promoters to drive expression of the non-native proteins. See U.S. Pat. Nos. 6,680,179 and 6,951,741.

The *Rhodospirillum* species may be any member of the *Rhodospirillum* genus, including, but not limited to, *Rhodospirillum rubrum, Rhodospirillum photometricum, Rhodospirillum molischianum, Rhodospirillum fulvum, Rhodospirillum salexigens, Rhodospirillum salinarum, Rhodospirillum mediosalinum, Rhodospirillum centenum*, and *Rhodospirillum sodomense*. Suitably, the *Rhodospirillum* species is *Rhodospirillum rubrum*.

Suitably, the *Rhodospirillum* species has reduced expression of at least one of the proteins natively associated with the ICM relative to wild-type *Rhodospirillum rubrum* or relative to the species from which it was derived. An exemplary wild-type *Rhodospirillum rubrum* strain (strain H1) is available as ATCC deposit number PTA-5207. For example, the *Rhodospirillum* species may have reduced expression of RC-H, RC-L, RC-M, LH-α, or LH-β. Reduced expression of the ICM protein may be achieved by manipulating the organism to disrupt a nucleic acid sequence encoding the protein. For example, the organism could be engineered to create a deletion, insertion, or frame-shift mutation in a nucleic acid encoding an ICM protein such that its expression is diminished as compared to a wild-type organism.

Alternatively, it is envisioned that naturally occurring *Rhodospirillum* isolates having reduced expression of a protein natively associated with ICM may be obtained and used in the practice of the present invention. Such naturally occurring isolates could be identified by a reduced ability to grow under phototrophic conditions or a reduced ability to produce the phototrophic apparatus. The phototrophic apparatus is pigmented so bacteria having a reduced ability to produce the phototrophic apparatus could be selected by screening for an inability to grow or for reduced pigmentation of the bacteria under phototrophic conditions. Those of skill in the art could envision multiple ways of generating bacteria with reduced expression of ICM proteins, for example site-directed or random mutagenesis, transposon mutagenesis, and also screening for natural variants.

Reduced expression of a protein natively associated with the ICM will allow incorporation of heterologous proteins into the ICM. Suitable *Rhodospirillum* species having reduced expression of an ICM protein include, but are not limited to, *Rhodospirillum rubrum* P5, *Rhodospirillum rubrum* P4, *Rhodospirillum rubrum* H15, *Rhodospirillum rubrum* H1, *Rhodospirillum rubrum* H2, *Rhodospirillum rubrum* M1, *Rhodospirillum rubrum* P41 and derivatives of any of these strains (TABLE 1).

TABLE 1

Suitable *Rhodospirillum* species according to the invention.

| Strain | Comments |
|---|---|
| P5 | pufBALM deletion, kanamycin cassette inserted; described in Hssner et al. |
| P4 | puf BALM deletion, chloramphenicol cassette inserted |
| H15 | puhA deletion, kanamycin cassette inserted; described in Cheng et al. 2000 |
| H1 | puhA, pufBALM deletions, kanamycin and chloramphenical cassettes inserted; deposited with ATCC |
| M1 | pufBALM unmarked deletion, as described in Example 1 |
| H2 | pufBALM, puhA unmarked deletions, as described in Example 1 |
| P41 | pufBALM unmarked deletion |

The puc promoter is suitably operably linked to a nucleic acid encoding a polypeptide such that the promoter drives expression of the polynucleotide and the polypeptide is produced. A nucleic acid encoding any polypeptide may be used in the vector. Suitably, the nucleic acid operably linked to the puc promoter encodes a membrane polypeptide that may be associated with the ICM. A membrane polypeptide includes integral membrane proteins, peripheral membrane proteins and proteins genetically engineered to contain a membrane spanning region.

A vector for expressing a polypeptide in a *Rhodospirillum* species includes the puc promoter. The vector may be a phage, plasmid, transposon or any other vector capable of delivering genetic material into *Rhodospirillum*. Suitably, the vector is capable of being maintained in *Rhodospirillum* and most suitably the vector is capable of replication in *Rhodospirillum*.

The puc promoter is suitably operably linked to a nucleic acid encoding a polypeptide such that the promoter drives expression of the polypeptide. A nucleic acid encoding any polypeptide may be used in the vector. Suitably, the nucleic acid operably linked to the puc promoter encodes a membrane polypeptide that may be associated with the ICM. A membrane polypeptide includes integral membrane proteins, peripheral membrane proteins and proteins genetically engineered to contain a membrane spanning region.

The vector may also contain selectable or screenable markers, a terminator fragment, a cloning site and an affinity tag. Selectable or screenable markers include, but are not limited to, antibiotic resistance genes, fluorescent protein markers, auxotrophic markers, and nutritional markers. In the Examples, ampicillin, chloramphenicol, gentamycin, and tetracycline were used as selectable markers in *Rhodospirillum*. Any suitable antibiotic resistance marker to which *Rhodospirillum* exhibits sensitivity may be used. In the Examples, the *Rhodospirillum rubrum* puh terminator fragment was used, but any other terminator fragment functional in *Rhodospirillum* may be used. A multiple cloning site may be inserted into the vector to enable easy insertion of nucleic acids encoding polypeptides such that the inserted nucleic acid will be operably linked to the puc promoter in the vector.

The vector may also contain an affinity tag, such as the histidine tag used in the Examples. Other affinity tags include, but are not limited to, maltose-binding protein, intein and peptide tags available from commercial suppliers such as Novagen (Madison, Wis.) and Amersham (Piscataway, N.J.). An affinity tag may be used to identify the protein using antibodies by techniques well-known to those of skill in the art such as western blotting or immunofluorescence. Additionally, an affinity tag may be used to isolate the polypeptide from the *Rhodospirillum* by any suitable method including those well known to those of skill in the art.

Another advantage of expressing polypeptides in the ICM of *Rhodospirillum* is relatively simple isolation of the polypeptide from the bacterium. As demonstrated in the Examples, the ICM can be enriched by disrupting the bacteria followed by differential centrifugation. The bacteria may be disrupted by any suitable method many of which are known to those of skill in the art including, but not limited to a French Press. The polypeptide may be further isolated from the *Rhodospirillum* by protein purification techniques, including those well-known to those of skill in the art. Due to the ease of isolation, the methods and systems described herein may be useful for expression and isolation of non-membrane associated polypeptides by linking these polypeptides to membrane spanning domains which may be subsequently removed by any suitable method, including those available to those of skill in the art. As used herein, isolation refers to separation of the ICM fraction containing the heterologous protein from the bacteria. Isolation does not require that the heterologous protein be purified, but only enriched.

The vector containing the puc promoter operably linked to a nucleic acid encoding a polypeptide may be introduced into the *Rhodospirillum* by any suitable method including but not limited to, transfection, transduction, transformation, conjugation, electroporation and particle bombardment. In the Examples, the vector was a plasmid that was introduced into the *Rhodospirillum* by conjugation. The method of introducing the vector will depend on the type of vector chosen as will be understood to those of skill in the art.

The *Rhodospirillum* species may be grown under conditions that allow expression of the polypeptide. The puc promoter is known to be induced by low light and reduced oxygen tension in *Rhodobacter capsulatus*. See Nickens and Bauer, J Bacteriol. (1998) 180: 4270. As one of skill in the art will appreciate, the oxygen tension may be reduced in a variety of ways, including growing cultures under reduced aeration, reducing the surface area to volume ratio of the cultures, growing the cultures to late log or stationary phase, or including at least one alternative electron acceptor in the cultures, or a combination thereof.

The puc promoter may be induced by growing the bacteria under semi-aerobic conditions. Semi-aerobic conditions can be achieved by growing the bacteria in flasks that are filled with media to at least about 70% capacity, suitably at least about 75% capacity, suitably about 80% capacity. The puc promoter may be induced by growing the bacterial cultures either without aeration (supplied by "shaking" the cultures) or with reduced shaking relative to that needed to provide aerobic culture conditions. Aerobic cultures are typically grown with shaking at about 300 rpm. Semi-aerobic cultures are suitably grown with shaking at less than about 300 rpm, suitably less than about 250 rpm and more suitably at less than about 220 rpm. Semi-aerobic cultures are suitably grown with shaking in a range of from about 100 rpm and to about 250 rpm, suitably the cultures are grown with shaking at least about 100 rpm, at least about 150 rpm or at least about 200 rpm and less than about 300 rpm. In the Examples, bacteria were grown semi-aerobically by filling an Erlenmeyer flask to 80% capacity with growth medium and shaking the culture at 200 rpm. As demonstrated in the Examples, the polypeptide is expressed when the *Rhodospirillum* is grown under aerobic conditions, but considerably higher expression is obtained in bacteria grown under semi-aerobic conditions. See FIG. 2 (Example 1).

Alternatively, the bacteria containing the vector including the puc promoter may be grown anaerobically in the presence of an alternative electron acceptor to induce the puc promoter. Alternative electron acceptors include, but are not limited to, dimethyl sulfoxide, methionine sulfoxide, trimethylamine oxide and combinations thereof. Alternatively, the puc promoter may be induced by growing the bacteria to late log phase. For *Rhodospirillum rubrum* late log phase is generally indicated when the culture has an optical density at 680 nm ($OD_{680\,nm}$) of greater than about 0.6.

In yet another aspect, a system for expressing a polypeptide is provided. The system includes a *Rhodospirillum* and a vector that contains the puc promoter. The vector in the system is similar to the vector described above, but the vector in the system does not require a nucleic acid encoding a polypeptide operably linked to the puc promoter. Suitably, the vector contains a cloning site into which a nucleic acid encoding a polypeptide can be readily cloned by are suitable methods including those known to those of skill in the art. The system allows for obtaining expression of any polypeptide of interest to a user of the system. The user can clone the nucleic acid encoding the polypeptide into the expression vector using any suitable method, may of which are well known to those of skill in the art such that the coding sequence is operably linked to the promoter. The user can then introduce the vector into *Rhodospirillum* and grow the *Rhodospirillum* under conditions that induce expression of the puc promoter as described above.

The following examples are meant for purposes of illustration only and are not meant to be limiting upon the scope of the invention.

EXAMPLES

Example 1

Expression and Purification of *P. aeruginosa* MscL from puhA, pufBALM Deletion Mutant *R. rubrum* H2

Cell Growth

Cultures were grown at 30° C. in Ormerod's medium (Ormerod, J. G. et al. (1961) Arch. Biochem. Biophys. 94: 449-463) modified with the addition of 0.1% yeast extract as described previously (Myers, C. R. et al. (1987) J. Bacteriol. 169: 5445-5451). *Escherichia coli* cultures were grown in Luria-Bertani medium (Sambrook, J. et al. (2001) Molecular Cloning a laboratory manual, Third Edition. Cold Spring Harbor Laboratory, Cold Spring Harbor, N.Y. 3: 1.112-1.115). For growth of *E. coli* WM3064 or *E. coli* β2155, the medium was supplemented with DL-α,ε-diaminopimelic acid. Where appropriate, antibiotics were added to the following final concentrations: ampicillin 50 μg/ml; rifampin 15 μg/ml; gentamycin 25 μg/ml, tetracycline 12.5 μg/ml. Synthesis of MscL was induced by semi-aerobic incubation. For this purpose, 300 mL aerobic cultures were first grown in 2.8 L Fernbach flasks with shaking at 300 rpm. For semi-aerobic conditions, cultures were transferred to Erlenmeyer flasks filled to 80% capacity and incubated at 30° C. with shaking at 200 rpm for 21-24 h. Bacterial strains and plasmid constructs used in this study are listed in Table 2.

Construction of *R. rubrum* H2

A puhA, pufBALM mutant was constructed by allelic exchange using the strategy previously described (Benson, J. A. 2007. Production and assembly of light-harvesting antenna in *Rhodospirillum rubrum*. M.S. thesis. University of Wisconsin-Milwaukee). A puhA deletion fragment was constructed by joining fragments flanking puhA that were amplified by PCR using primers P5 and P6 for the upstream fragment and P7 and P8 for the downstream fragment (Table 3). These fragments were joined by ligation into pGEM-3Z to form a deletion fragment that was subcloned into the suicide vector pZJD29a. This construct was introduced into *R. rubrum* R5 by conjugation and transconjugants with the plasmid crossed into the chromosome were selected on gentamycin. This was followed by sucrose selection for a second cross-over event. The sequence of the mutated region in the resulting strain *R. rubrum* M1 was verified and is shown in Table 4. A pufBALM deletion fragment was used previously for the construction of *R. rubrum* P41 (Benson, J. A. 2007. Production and assembly of light-harvesting antenna in *Rhodospirillum rubrum*. M.S. thesis. University of Wisconsin-Milwaukee). This fragment was exchanged into the chromosome of *R. rubrum* M1 using pZJD29a. The sequence of the puf-deleted region of the resulting puhA, pufBALM strain H2 was verified and is shown in Table 4.

TABLE 2

Strains and constructs used in this study.

| Strain or Construct | Characteristics | Source |
|---|---|---|
| *R. rubrum* R5 | resistant to rifampin; wild type with respect to puhA and puf; parental strain for M1 and H2 | Hessner et al. |
| *R. rubrum* M1 | puhA mutant | Example 1 |
| *R. rubrum* H2 | pufA, pufBALM mutant | Example 1 |
| *E. coli* WM3064 | conjugation donor | W.W. Metcalf |
| *E. coli* β2155 | conjugation donor | Dehio and Meyer |
| pBBR1MCS-3 | broad-host-range vector, tetracycline resistance | Kovach et al. |
| pPUCTerm | expression vector | Example 1 |
| pPUCMscL | vector for expression of mscL | Example 1 |
| pPTMscL | control plasmid lacking promoter | Example 1 |
| pET-DEST42-MscL_V5_6his Msc | *P. aeruginosa* mscL clone | Connie Jeffery, University of Illinois, Chicago |
| pBACDE | *R. capsulatus* pucBACDE clone | Le Blanc et al. |
| pH3.6- | clone of *R. rubrum* puhA and flanking regions | Cheng et al. |
| pZJD29a | suicide vector, sacB, gentamycin resistance | Masuda et al. Yano et al. |
| pGEM-3Z | cloning vector, ampicillin resistance | Promega Corp. |
| pSTBlue-1 | cloning vector, ampicillin resistance | EMD Novagen, Inc |

TABLE 3

Primers used in construction of vectors.

puc promoter sequence:

pucu1   SEQ ID NO: 3
        5'CCCTCTAGAGCGACAGGATCGTCCTTG pucu2   SEQ ID NO: 4
        5'CCCTCTAGATTTGCAGCATGGCTCTTGC pucd    SEQ ID NO: 5
        5'AAACTCGAGCAAAACTGGGATCATTGG terminator sequence

TF1     SEQ ID NO: 6
        5'GTAATTGGGGCATGCCACATGGATGA

TR1     SEQ ID NO: 7
        5'CGGCGGTCAGAAGCTTGGGCAGCGGAT primers used to amplify polynucleotide encoding MscL protein mscf    SEQ ID NO: 8
        5'GGCAAGAATTAGGAGGTAGCACCTATGGGTCTTCTGAGTGAA
        TTC mscr    SEQ ID NO: 9
        5'TCATCAATGATGATGATGATGATGCGACTTGTTCTGCTGGGC
        sequence encoding hexahistidine
        tag underlined msclf2  SEQ ID NO: 10
        5' GGGCAAGAATTAGGAGGTAGCACCT ATG GGT
        CTT CTG AGT GAA primers to amplify puhA flanking regions:

P5      SEQ ID NO: 11
        5' GAGCTCGCCCTTCGCCCTGTTCGTCC
        SacI site underlined

TABLE 3-continued

Primers used in construction of vectors.

| | | |
|---|---|---|
| P6 | SEQ ID NO: 12 | 5' ATAC<u>GACGT</u>CATGGAAGTATGCCGCCAACGAGGAAACGCC<br>AatII site underlined |
| P7 | SEQ ID NO: 13 | 5' ATACTTCCAT<u>GACGT</u>CGTATCCTTGCCCTCCGGGTGTTTC<br>AatII site underlined |
| P8 | SEQ ID NO: 14 | 5' <u>CTCGAG</u>TCGCCGCCACGCCGATCCGC<br>XhoI site underlined |

TABLE 4

Sequences of mutant strains constructed in this study[a].

M1 puhA-deleted region[b] (SEQ ID NO: 21)

GAATGGCGCTCGGCGCTTGGGGCGCCGTGCAGGCCACCGCGACCGGC

GCGGCCGTTGCCCTTGGCGGCGGCTTGCGCGATGGCGTTTCCTCGTTGG

CGGCATACTTCCATGACGTCCCTTGCCCTCCGGGTGTTTCACATTCGGC

TGATCGCGCTTTATTTCGCGATTCTGGTGGCGTGGAACGTGGCCTCGGC

TTTGTATGACGGCCATCCGCTG

H2 pufBALM-deleted region (SEQ ID NO: 22)

CGCGACGCCGCCGAGCGCAGCGCCCGGGCGGCGGGTGAAGGACAGGT

TACGGCGGCGCGGGTTATCCGCCTGCTCGATCTTCAGGCTGGAGCGTA

AGGGCGACTTGGAGCACGACGCTCCGGCCTGAGCTTGATCGCATAGCC

TACCGTCCTTGATCGCCTCGCGGCGGAACAGGACCTACGGGCGGGAA

TGGTCGAACAGACCGTTCTCGCCCTGTTGC

[a]sequences shown extend from 100 bp upstream of deletion to 100 bp downstream of the deletion.
[b]M1 is the parent strain of H2.

Plasmid Construction

The plasmid pPUCMscL was constructed by cloning the *Rhodobacter capsulatus* puc promoter fragment, the *Pseudomonas aeruginosa* mscL structural gene, and the *R. rubrum* puhA terminator fragment into pBBR1MCS-3. The puhA terminator fragment was amplified with primers TF1 and TR1 (Table 3) using pH3.6—as a template and cloned into pSTBlue-1 (Novagen). The terminator fragment was excised by digestion with SphI and HindIII and the resulting fragment treated with T4 Polymerase (Promega) to create blunt ends. This fragment was cloned into pBBR1MCS-3 to construct pBBRTerm. For this purpose, pBBR1MSC-3 was digested with KpnI (Promega) and treated with T4 Polymerase (Promega) and shrimp alkaline phosphatase (Promega) to make blunt, dephosphorylated ends.

The mscL structural gene was amplified with primers mscf and mscr (Table 3) using the gene cloned into pET-DEST42-MscL_V5_6his Msc (See Table 2) as a template. The primer mscr introduced a hexahistidine tag. The amplified fragment was treated with T4 polynucleotide kinase (Promega) and cloned into pBBRTerm that had been digested with XhoI (Promega), treated with T4 polymerase, and dephosphorylated with Antartic phosphatase (New England Biolabs) forming the construct pPTM.

The puc promoter was amplified with the primers pucd and pucu2 (Table 3) using pBACDE (See Table 2) as a template.

The puc fragment (SEQ ID NO: 2) was digested with XhoI and XbaI (Promega) and cloned into pPTM and pBBRTerm that had been digested with these enzymes. The resulting clones are pPUCMscL and pPUCTerm (SEQ ID NO:25) respectively; the former is the expression plasmid for mscL, while the latter is the expression vector lacking the mscL structural gene.

A control plasmid with the mscL gene but lacking the promoter was constructed by amplifying mscL with the primers msclf2 and mscr (Table 3) and cloning the resulting PCR product into pBBRTerm cut with SmaI. The resulting plasmid was named pPTMscL.

A similar strategy was employed to generate pPUCLGMscL which includes the puc promoter of SEQ ID NO:1. The only difference was that the puc promoter was amplified using pucul and pucd. The puc fragment was digested and cloned as above.

Cell Fractionation

Cells were harvested, and broken in the French pressure cell to prepare cell-free extracts as previously described (Mueller et al. (1983) J. Bacteriol. 153: 1562-1566). The cell-free extract was fractionated by differential centrifugation. For this purpose, the cell extract was centrifuged at 12,000 rpm (18,000×g) in a JA-20 rotor (Beckman Coulter) to pellet the cell envelope fraction. The supernatant fraction was centrifuged at 50,000 rpm (230,000×g) for 2 h in a Type 70.1 Ti rotor in an Optima L-90K ultracentrifuge (Beckman Coulter) to recover the ICM-enriched fraction.

Western Blots

Western immunoblots were performed essentially as described previously (Brantner et al (2002) Arch Microbiol. 178: 59-64). Primary antibody was anti-His tag monoclonal antibody (EMD Biosciences). Secondary antibody was goat-anti-mouse Ig conjugated to horseradish peroxidase (Southern Biotech). Blots were developed with Pierce Super Signal West Pico Chemiluminescent substrate (Thermo Fisher Scientific).

Electron Microscopy

Cells were prepared for electron microscopy as described previously (Brantner et al (2002) Arch Microbiol. 178: 59-64; Collins et al. (1991) Appl. Environ. Microbiol. 57: 1261-1264). Briefly, cells were fixed in 0.5% gluaraldehyde, post-fixed in 1% $OsO_4$, dehydrated in a graded ethanol series, embedded in LR White (Electron Microscopy Sciences), sectioned and post-stained with aqueous 1% uranyl acetate.

Preparation of MscL Protein

H2 (pPUCMscL) was grown to an $OD_{680\,nm}$ of 1.7 then incubated under semiaerobic conditions for 24 h. Cells were harvested, washed in 20 mM sodium phosphate, 500 mM NaCl, pH 7.4. After addition of 5 µl/ml protease inhibitor (Protease Inhibitor Cocktail, set III, EMB Chemicals, Inc., San Diego Calif.), cells were broken by 2 passages through the French press at 16,000 psi. After unbroken cells were removed by centrifugation at 750×g for 10 min, the crude membrane fraction (CMF) was pelleted at 230,000×g for 2 h. The pellet was resuspended in buffer with protease inhibitor and solubilized by treatment for 1 h at 4° C. with dodecyl-maltoside (DDM, Anatrace) at a detergent protein ratio of 6:1. The insoluble fraction was sedimented at 230,000×g in 2 h. MscL was purified from the DDM extract using His SpinTrap (GE Healthcare) or Profinity IMAC Ni-charged resin (Bio-Rad Laboratories). Prior to application to the column, the extract was diluted in buffer to a DDM concentration <1%. The sample was applied in buffer with 20 mM imidazole and eluted with 500 mM imidazole. Protein concentration was measured with either the Pierce BCA Protein Assay or Pierce Coomassie+ kits (Thermo Fisher Scientific).

Electron Microscopy of R. rubrum H2 with pPUCTerm and pPUCMscL

The puhA, pufBALM deletion mutant R. rubrum H2 lacks the photochemical apparatus. Electron micrographs of ultrathin sections of R. rubrum H2 strains incubated under semi-aerobic conditions suggest that the puhA, pufBALM deletion mutant R. rubrum H2 does not form ICM (H2, pPUCTerm; FIG. 1A) under semi-aerobic conditions which induce the formation of ICM in the wild type. ICM was observed on the cells with pPUCMscL producing MscL (FIG. 1B-E). The ICM is lamellar in structure and abundant at the cell periphery. In oblique sections the ICM can be seen (FIG. 1D). No ICM was observed in the vector control. These results suggest that ICM is only formed when MscL is produced.

MscL can be Detected by Western Blot

Figure 2:
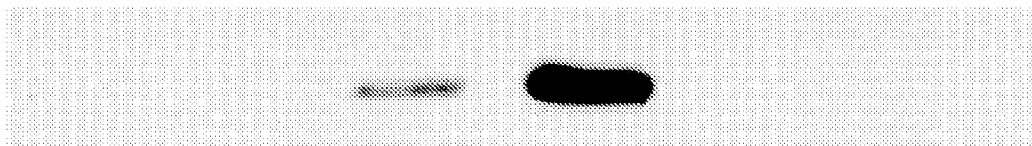
FIG. 2 is a digital image of a western blot showing expression of MscL in *R. rubrum* incubated under either aerobic (odd numbered lanes) or semi-aerobic (even numbered lanes) conditions from plasmids with no promoter (pPTMscL, lanes 1 and 2), the short puc promoter (pPUCMscL, lanes 3 and 4) or the short puc promoter without the mscL gene (pPUCTerm, lanes 5 and 6).

MscL was detected in H2 (pPUCMscL) by western blot (lanes 3 and 4 of FIG. 2). No MscL was detected in the vector control H2 (pPUCTerm, lanes 5 and 6 of FIG. 2) or in the strain with a construct lacking the puc promoter H2 (pPTMscL, lanes 1 and 2 of FIG. 2) indicating that mscL expression was driven by the R. capsulatus puc promoter. While some MscL was produced under aerobic conditions (lane 3 of FIG. 2), production was induced by incubation under semi-aerobic conditions (lane 4 of FIG. 2). No differences in regulation or expression level were obtained using the longer puc promoter of pPUCLGMscL. Therefore all subsequent experiments used the shorter puc promoter.

MscL Localizes to the ICM

Figure 3:
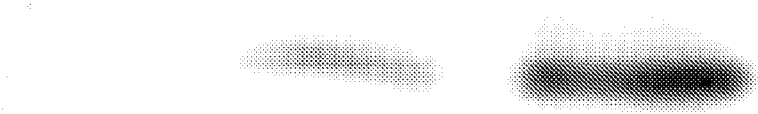
FIG. 3 is a digital image of a western blot showing the intracellular localization of MscL in *R. rubrum* strains carrying pPUCMscL. Lane 1 is the supernatant fraction, lane 2 is the 18,000×g pellet, and lane 3 is the 230,000×g pellet.

H2 (pPUCMscL) cells were fractionated to assess the intracellular localization of MscL. No MscL was detected in the supernatant fraction (FIG. 3, lane 1). MscL was detected in both the cell envelope (FIG. 3, lane 2) and ICM fractions (FIG. 3, lane 3), but was enriched in the ICM fraction.

Isolation of MscL

Figure 4:
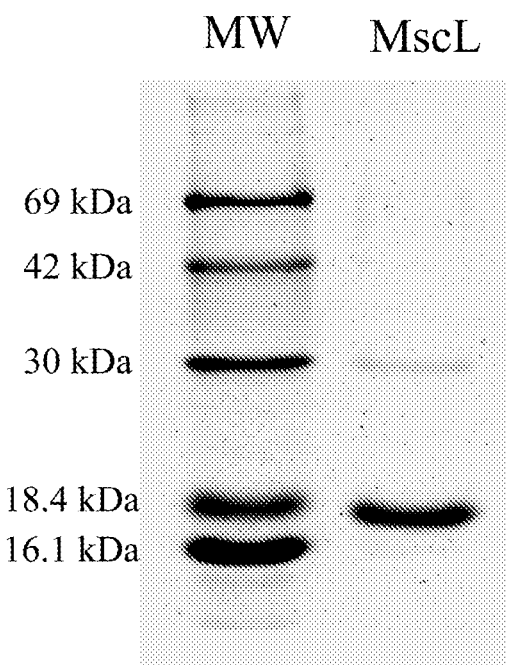
FIG. 4 is an SDS-PAGE gel of molecular weight standards (MW) and MscL protein purified by immobilized metal affinity chromatography (IMAC).

As described above, MscL was purified from the membranes of H2 (pPUCMscL) induced by incubation under semi-aerobic conditions. Crude membranes were recovered from the cell-free extract and membrane proteins were solubilized by treatment with DDM. MscL was purified from the DDM-extracted proteins by immobilized metal affinity chromatography (IMAC). SDS-PAGE analysis (FIG. 4) of the eluted protein revealed a band with an apparent molecular weight of 17 kDa; MscL with the hexahistidine tag is 15.5 kDa. Amino-terminal sequencing confirmed the identity of this protein as P. aeruginosa MscL. A minor band with an apparent molecular weight of 30 kDa was also observed. Amino-terminal sequencing of this band indicated that it is also formed by MscL and is apparently a dimer. This band was observed whether or not the samples were heated prior to electrophoresis. The dimer (and larger oligomers) was observed on SDS-PAGE without heat treatment indicating that these are not artifacts but multimers that are present even in the presence of SDS and dithiothreitol. Native MscL is a homopentomer, indicating that the purified MscL proteins have retained their oligomerization capacity. The protein was assessed to be >99% pure, as no other bands were observed in the SDS-PAGE gel. In repeated experiments, the yield of purified MscL produced in R. rubrum was 16-21 mg/L culture and 3.8 mg/g cell paste.

Comparison of Protein Yield with R. rubrum and E. coli

Figure 5:
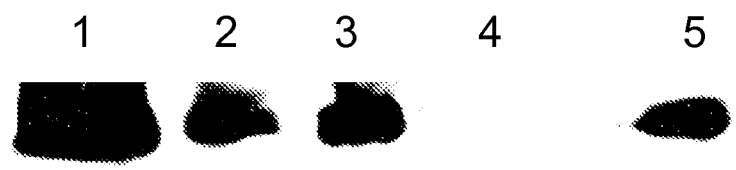
FIG. 5 is a digital image of a western blot showing detection of MscL in fractions from *E. coli* (lanes 1-4) and *R. rubrum* (lane 5).

An E. coli C43(DE3) clone expressing MscL was obtained from Dr. C. Jeffery at the University of Illinois at Chicago. This strain was grown in LB medium to mid log phase and induced by the addition of arabinose to a final concentration of 0.2% and IPTG to a final concentration of 1 M. A CMF was prepared, and a detergent extraction and purification were performed as described above. No MscL could be detected in the IMAC eluate. However, MscL was detected by western blot of cells, in the CMF, and in the 2500 rpm pellet (FIG. 5; lane 1, 2500 rpm pellet from E. coli; lane 2, 230,000×g E. coli supernatant fraction; lane 3, 230,000×g E. coli pellet (CMF); lane 4, DDM-solubilized fraction from E. coli; lane 5, 230, 000×g R. rubrum H2 pellet (CMF)). The presence of MscL in the latter fraction suggested that it was present in inclusion bodies. The MscL content of the solubilized membrane protein was low, consistent with its presence in inclusion bodies that would not be solubilized by detergent. The MscL content of the CMF of R. rubrum H2 was 2 orders of magnitude greater than that of E. coli.

Example 2

Expression and Purification of Pseudomonas Cytochrome $B_{561}$ (CycB) in R. rubrum H2

The structural gene for CycB was amplified by PCR using the plasmid pDONR201-CycB/20 (obtained from C. Jeffery, University of Illinois, Chicago) as a template. This plasmid was obtained from Constance Jeffery at the University of Illinois, Chicago. The primers used were CytF (SEQ ID NO:15) and CytR (SEQ ID NO:16) as shown in Table 5. The amplified fragment encoding CycB (SEQ ID NO:26) with a $His_6$ tag was treated with T4 polynucleotide kinase (Promega) and cloned into pBBRTerm (described above in Example 1) that had been digested with XhoI (Promega), treated with T4 polymerase, and dephosphorylated with Antartic phosphatase (New England Biolabs). The puc promoter was amplified with the primers pucd and pucu2 as described above. The puc fragment was digested with XhoI and XbaI (Promega) and cloned into the vector that had been digested with these enzymes forming the construct pPUCCycB. pPUCCycB was introduced into R. rubrum by conjugation, according to Example 1 above. CycB from P. aeruginosa was purified from membranes prepared from H2, and membrane protein was solubilized under the same conditions used for MscL and purified by IMAC as described above in Example 1, with the exception that the extract was applied to the purification column in either 40 mM or 60 mM imidazole and eluted with 500 mM imidazole buffer.

TABLE 5

Primers used to amplify the polynucleotide encoding Pseudomonas cytochrome $B_{561}$.

Primers

CytF SEQ ID NO: 15  5' GCAAGAATTAGGAGGTAGCACCTATGAGCTGGAAA AACACCG

CytR SEQ ID NO: 16  5' TCATCAATGATGATGATGATGATGGCGCCGTTGGGG GAGCATC

Figure 6:
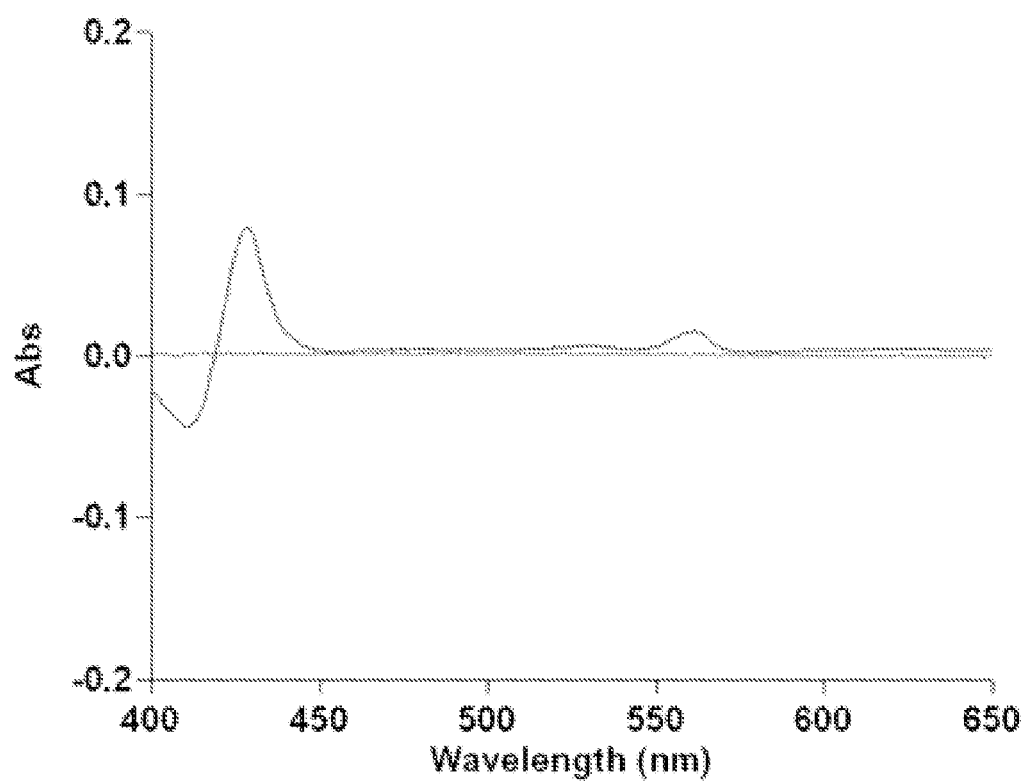
FIG. 6 is a reduced-minus-oxidized difference spectrum of *P. aeruginosa* cytochrome $b_{561}$ produced in *R. rubrum*, with the characteristic peak at 561 nm.

The recovery of CycB purifed with 40 mM imidazole was 1 g/L culture (0.17 mg/g cell paste). When analyzed on SDS-PAGE, the migration of the protein band corresponded to the predicted molecular weight of CycB and the identity of the protein was confirmed by mass spectrometry. Additionally, heme peroxidase activity was detected in the sample by spotting the purified CycB sample on nitrocellulose and treating with Pierce Super Signal West Pico according the method of Feissner et al (2003). The purified protein was also characterized spectrally and exhibited the characteristic reduced-minus-oxidized difference spectrum (FIG. 6). These results suggested that the heterologous cytochrome was properly assembled with its heme cofactor in the R. rubrum host and has heme peroxidase activity.

Example 3

Expression and Purification of KcsA

The structural gene for *Streptomyces lividans* KcsA was amplified by PCR using the plasmid pQE32-KcsA as a template (provided by R. Viola at the University of Toledo). The primers used were KcsF (SEQ ID NO:19) and KcsR (SEQ ID NO:20) as shown in Table 6. These primers introduced XhoI and ApaI sites. The amplified fragment was phosphorylated and cloned into SmaI-cut pGEM3Z. The KcsA-encoding fragment was excised from the latter construct with ApaI and XhoI and ligated into pPUCTerm (described above in Example 1) digested with these enzymes to create the expression vector encoding KcsA with a His$_7$ tag. The expression vector was introduced into R. rubrum H2 by conjugation, according to Example 1 above.

TABLE 6

Primers used to amplify the polynucleotide encoding *Streptomyces lividans* KcsA.
Primers KcsF SEQ ID 5' CTCGAGGGCAAGAATTAGGAGGTAGCACCTATGCCG
NO: 19 CCCATGCTGTCCGGTCTTCTGGCCCGCTTGG KcsR SEQ ID 5' GGGCCCTCATCAATGATGATGATGATGATGATGCCG
NO: 20 GCGGTTGTCGTCGAGCATGCGCTCC R. rubrum H2 cultures including the expression vector encoding KcsA were grown in 300 mL cultures in 2.8 L Fernbach flasks to an OD680 nm>1. Cultures were induced by reduction of oxygen tension by incubation in Erlenmeyer flasks filled to 80% capacity and incubated at a low shake rate. After 24 hr, cells were harvested and washed. A sample was retained for whole cell western analysis and the remainder broken in the French Press. Unbroken cells and debris were removed by centrifugation at 2500 rpm in 10 min. The supernatant fraction was centrifuged at 230,000×g for 2 hr. The pellet from this centrifugation was termed the crude membrane fraction (CMF) and stored at −75° C. For solubilization of membrane proteins, the CMF was thawed and treated with dodecyl maltoside (DDM) at a detergent:protein ratio of 6:1. The detergent extraction was incubated for 1 hr at 4° C. and the insoluble fraction was recovered by ultracentrifugation.

The detergent extract was diluted to a DDM concentration of 1% and was fractionated by IMAC. This was accomplished by using spin columns.

Figure 7:
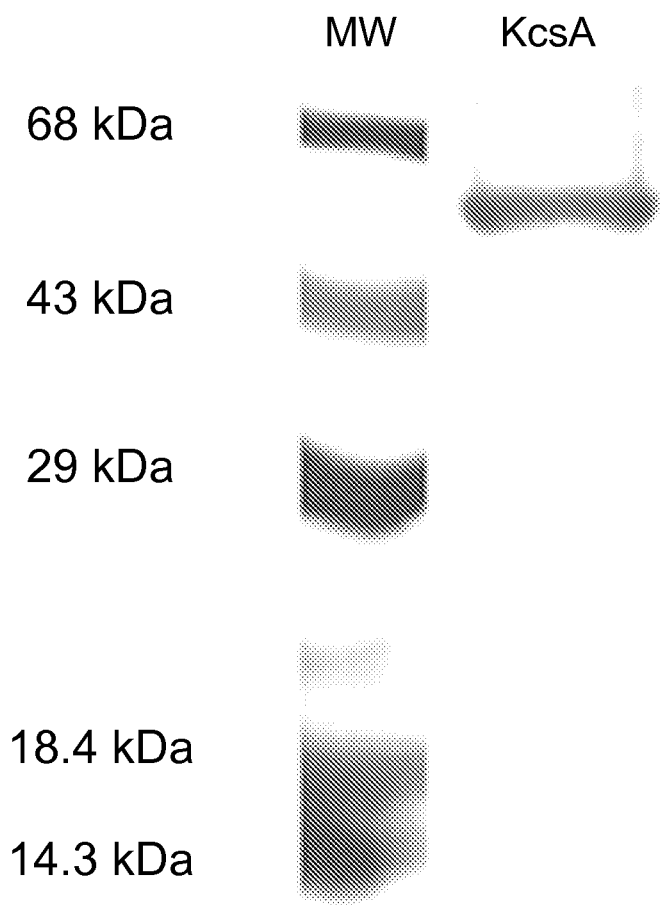
FIG. 7 is an SDS-PAGE gel of molecular weight standards (MW) and KscA protein purified by IMAC.

KscA was purified with a yield of 3.49 mg/L and 0.62 mg/g cell paste. This is an underestimate as some KcsA was present in the flow-though. KcsA was designed with a 7 His tag. Sample was applied to IMAC spin columns and the column was washed in 40 mM imidazole and eluted with 500 mM imidazole. Under these conditions, the product was >99% pure as judged by SDS-PAGE (FIG. 7). When 20 mM imidazole was used, the total protein yield was higher (4.9 mg/L) but the product was not pure. KcsA was present as an oligomer when samples were not boiled prior to SDS-PAGE; KcsA was monomerized by boiling prior to electrophoresis. The identity of the band in the SDS-PAGE gel was confirmed by amino-terminal sequencing and western blot analysis.

KscA has been previously purified from *E. coli* by another lab, and 4.5 mg/L of a KcsA preparation was obtained that was 75% pure (personal communication, R. Viola, University of Toledo). This is comparable to the yield achieved with R. rubrum on a per L basis. Since *E. coli* grows to a higher density, the yield was less than that obtained with R. rubrum on a per g cell paste basis.

Example 4

Western Blot Detection of Heterologous Membrane Proteins Produced in R. rubrum

Other membrane proteins were successfully expressed in R. rubrum H2 (Table 7). The tabulated proteins (Table 7) were expressed as described in Example 1. A C-terminal His tag was introduced, and the proteins were detected by western blots of whole cells with anti-His antibody as described in Example 1.

TABLE 7

Proteins expressed in R. rubrum H2 as detected by western blot

| protein | source | kDa* | TM domains | cofactor | biological role | comments |
|---|---|---|---|---|---|---|
| MscL | Pseudomonas | 15.3 | 2/monomer | | ion channel | homopentomer |
| CycB | Pseudomonas | 21.4 | 2-4 predicted | heme | redox | |
| PhoR | Pseudomonas | 50.9 | 2 | | receptor kinase | |
| KcsA | Streptomyces | 18.7 | 2/monomer | | K+ channel | homotetramer, shaker |
| A1 | human | 38.5 | 7 | | GPCR | drug target |
| MAO B monoamine oxidase B | human | 60.6 | 1 | flavin | deamination of monoamines | drug target, outer mitochonrial membrane |
| HCYC Cytb$_{561}$ | human | 29.4 | 6 | heme | catecholamine biosynthesis | |

*includes affinity tag

PhoR

The polynucleotide encoding PhoR (SEQ ID NO:30) was amplified by PCR using the plasmid pET-DEST42-PhoR-V5_6his (obtained from C. Jeffery, University of Illinois, Chicago) as a template. The primers used were phof (SEQ ID NO:17) and phor (SEQ ID NO:18) as shown in Table 8. The amplified fragment encoding PhoR with a His$_6$ tag was treated with T4 polynucleotide kinase (Promega) and cloned into pBBRTerm (described above in Example 1) that had been digested with XhoI (Promega), treated with T4 polymerase, and dephosphorylated with Antartic phosphatase (New England Biolabs). The puc promoter was amplified and cloned into the vector as described above forming the construct pPUCPhoR.

TABLE 8

Primers used to amplify the polynucleotide encoding PhoR.
Primers

| | | |
|---|---|---|
| phof | SEQ ID NO: 17 | 5' GGCAAGAATTAGGAGGTAGCACCTATGCAATCCGT CGTGAACC |
| phor | SEQ ID NO: 18 | 5' TCATCAATGATGATGATGATGATGCTTCGGGGCCT TGCGCTCG |

*R. rubrum* H2 cultures of the strain bearing this expression vector encoding PhoR were grown in 300 mL cultures in 2.8 L Fernbach flasks. Cultures were induced by reduction of oxygen tension by incubation in Erlenmeyer flasks filled to 80% capacity and incubated at a low shake rate. After 24 hr, cells were harvested and washed. Using the methods described above in Example 1, the presence of PhoR was confirmed by western blot analysis.

Human Monamine Oxidase B (MAO B)

The polynucleotide encoding MAO B (SEQ ID NO:23) was chemically synthesized to optimize codon usage. This DNA fragment was synthesized with an XhoI and an ApaI site near the termini. The fragment was trimmed by cleavage with these enzymes and cloned into the expression vector pPUC-Term (Example 1) cut with XhoI and ApaI.

The expression vector was introduced into *R. rubrum* by conjugation, according to Example 1 above. *R. rubrum* cultures of the strain bearing the expression vector encoding MAO B were grown in 300 mL cultures in 2.8 L Fernbach flasks. Cultures were induced by reduction of oxygen tension by incubation in Erlenmeyer flasks filled to 80% capacity and incubated at a low shake rate. After 24 hr, cells were harvested and washed. Using the methods described above in Example 1, the presence of MAO B was confirmed by western blot analysis.

Human Cytochrome $b_{561}$ (HCYC)

The polynucleotide encoding HCYC (SEQ ID NO:24) was chemically synthesized to optimize codon usage. This DNA fragment was synthesized with an XhoI and an ApaI site near the termini. The fragment was trimmed by cleavage with these enzymes and cloned into the expression vector pPUC-Term (Example 1) cut with XhoI and ApaI.

The expression vector was introduced into *R. rubrum* H2 by conjugation, according to Example 1 above. *R. rubrum* cultures of the strain bearing the expression vector encoding HCYC were grown in 300 mL cultures in 2.8 L Fernbach flasks. Cultures were induced by reduction of oxygen tension by incubation in Erlenmeyer flasks filled to 80% capacity and incubated at a low shake rate. After 24 hr, cells were harvested and washed. Using the methods described above in Example 1, the presence of HCYC was confirmed by western blot analysis.

After a sample was retained for whole cell western analysis, the remainder was broken in the French Press. Unbroken cells and debris were removed by centrifugation at 2500 rpm in 10 min. The supernatant fraction was centrifuged at 230,000×g for 2 hr. The pellet from this centrifugation was termed the crude membrane fraction (CMF) and stored at −75° C. For solubilization of membrane proteins, the CMF was thawed and treated with dodecyl maltoside (DDM) at a detergent:protein ratio of 6:1. The detergent extraction was incubated for 1 hr at 4° C. and the insoluble fraction was recovered by ultracentrifugation. The detergent extract was diluted to a DDM concentration of 1% and was fractionated by IMAC. This was accomplished on a small scale by spin columns.

A fraction containing HCYC obtained by IMAC exhibited heme peroxidase activity, and a Soret band was detected in the reduced-minus-oxidized difference spectrum.

Human Adenosine Receptor A1

The polynucleotide sequence encoding A1 (SEQ ID NO:27) was amplified by PCR using the plasmid ADRA100000 obtained from John Auchampach of the Medical College of Wisconsin) as a template. The primers used were ADORA1Kpnpuf5 (SEQ ID NO:28) and A1HFR (SEQ ID NO:29) as shown in Table 9. The amplified fragment encoding A1 with a $His_6$ tag was treated and cloned into the vector pBBRTerm and the puc promoter was cloned into the resulting construct, as described in Example 1.

TABLE 9

Primers used to amplify the polynucleotide encoding A1.
Primers

| | | |
|---|---|---|
| ADORA1K pnpuf5 | SEQ ID NO: 28 | 5' GGTACCGGCAAGAATTAGGAGGTAGCAC CTATGCCGCCCTCCATCTCAGCTTTCCAG |
| A1HFR | SEQ ID NO: 29 | 5' GCACTGCAGTCATCACTTATCATCATCGTCC TTATAGTCGGTGCCATGGTGATGATGATGATGGTCA TCAGGCCTCTCTT |

*R. rubrum* H2 cultures of the strain bearing this expression vector encoding A1 were grown in 300 mL cultures in 2.8 L Fernbach flasks. Cultures were induced by reduction of oxygen tension by incubation in Erlenmeyer flasks filled to 80% capacity and incubated at a low shake rate. After 24 hr, cells were harvested and washed. Using the methods described above in Example 1, the presence of A1 was confirmed by western blot analysis.

REFERENCES

Arechaga, I, B. Miroux, S. Karrasch, R. Huijbregts, B. de Kruijff, M. J. Runswick, and J. E. Walker. 2000. Characterization of new intracellular membranes in *Escherichia coli* accompanying large over-production of the b subunit of the $F_1F_0$ ATP synthase. FEBS Lett. 482: 215-219.

Benson, J. A. 2007. Production and assembly of light-harvesting antenna in *Rhodospirillum rubrum*. M.S. thesis. University of Wisconsin-Milwaukee.

Brantner, C. A., C. C. Remsen, H. A. Owen, L. A. Buchholz, and M. L. P. Collins. 2002. Intracellular localization of the particulate methane monooxygenase and methanol dehydrogenase in *Methylomicrobium album* BG8. Arch Microbiol. 178: 59-64.

Butzin, N. C. 2005. Development of methodology to identify promoters and use sacB selection to construct knockout mutants in *Rhodospirillum rubrum*. M.S. thesis, University of Wisconsin-Milwaukee. 21-24, 28-29, 36-45.

Chang, G., R. Spencer, A. T. Lee, M. T. Barclay, D. C. Rees. 1998. Structure of the MscL homolog from *Mycobacterium tuberculosis*: A gated mechanosensitive ion channel. Science 282: 2220-2226.

Cheng, Y. S., C. A. Brantner, A. Tsapin, and M. L. P. Collins. 2000. Role of the H protein in assembly of the photochemical reaction center and intracytoplasmic membrane in *Rhodospirillum rubrum*. J. Bacteriol. 182: 1200-1207.

Collins, M. L. P., L. A. Buchholz, and C. C. Remsen. 1991. Effect of copper on *Methylomonas albus* BG8. Appl. Environ. Microbiol. 57: 1261-1264.

Collins, M. L. P. and C. C. Remsen. 1990. The purple phototrophic bacteria, p. 49-77. In J. F. Stolz (ed.), Structure of Phototrophic Prokaryotes. CRC Press, Boca Raton.

Crook, S. M., S. B. Treml, and M. L. P. Collins. 1986. Immunocytochemical ultrastructural analysis of chromatophore membrane formation in *Rhodospirillum rubrum*. J. Bacteriol. 167: 89-95.

Dehio C and M. Meyer. 1997. Maintenance of broad-host-range incompatibility group P and group Q plasmids and transposition of Tn5 in *Bartonella henselae* following conjugal plasmid transfer from *Escherichia coli*. J. Bacteriol. 179:538-540

Hessner, M. J., P. J. Wejksnora, and M. L. P. Collins. 1991. Construction, characterization, and complementation of *Rhodospirillum rubrum* puf region mutants. J. Bacteriol. 173: 5712-5722.

Holt, S. C. and A. G. Marr. 1965. Location of chlorophyll in *Rhodospirillum rubrum*. J. Bacteriol. 89: 1402-1412.

Jester, B. C. 1998. Construction and characterization of a puf null mutant of *Rhodospirillum rubrum*. M.S. thesis, University of Wisconsin-Milwaukee. 18-26.

Kovach, M. E. P. H. Elzer, D. S. Hill, G. T. Robertson, M. A. Farris, R. M. Roop, and K. M. Peterson. 1995. Four new derivatives of the broad-host-range cloning vector pBBR1MCS, carrying different antibiotic-resistance cassettes. Gene 166: 175-176.

LeBlanc, H. N., and J. T. Beatty. 1993. *Rhodobacter capsulatus* puc operon: promoter location, transcript sizes and effects of deletion on photosynthetic growth. J. Gen. Microbiol. 139: 101-109.

Lefman, J., P. Zhang, T. Hirai, R. M. Weis, J. Juliani, D. Bliss, M. Kessel, E. Bos, P. J. Peters, and S. Subramaniam. 2004. Three-dimensional electron microscopic imaging of membrane invaginations in *Escherichia coli* overproducing the chemotaxis receptor Tsr. J. Bacteriol. 186: 5052-5061.

Masuda, S, and C. E. Bauer. 2004. Null mutation of HvrA compensates for loss of an essential relA/spoT-like gene in *Rhodobacter capsulatus*. J. Bacteriol. 186: 235-239.

Mueller, P. R. and M. L. P. Collins. 1983. Identification of two distinct lactate dehydrogenases in *Rhodospirillum rubrum*. J. Bacteriol. 153: 1562-1566.

Myers, C. R. and M. L. P. Collins. 1986. Cell-cycle-specific oscillation in the composition of chromatophore membrane in *Rhodospirillum rubrum*. J. Bacteriol. 166: 818-823.

Myers, C. R. and M. L. P. Collins. 1987. Cell-cycle-specific fluctuation in cytoplasmic membrane composition in aerobically grown *Rhodospirillum rubrum*. J. Bateriol. 169: 5445-5451.

Nickens, D. G. and C. E. Bauer. 1998. Analysis of the puc operon from *Rhodobacter capsulatus*. J. Bacteriol. 180: 4270-4277.

Nieboer, M, J. Kingma, and B. Witholt. 1993. The alkane oxidation system of *Pseudomonas oleovarans*: Induction of the alk genes in *Escherichia coli* W3110(pGEc47) affects membrane biogenesis and results in overexpression of alkane hydroxylase in a distinct cytoplasmic membrane subfraction. Mol. Microbiol. 8: 1039-1051.

Ormerod, J. G., K. S. Ormerod, and H. Gest. 1961. Light-dependent utilization of organic compounds and photoproduction of molecular hydrogen by photosynthetic bacteria; relationships with nitrogen metabolism. Arch. Biochem. Biophys. 94: 449-463.

Sambrook, J. and D. W. Russel. 2001. Molecular Cloning a laboratory manual, Third Edition. Cold Spring Harbor Laboratory, Cold Spring Harbor, N.Y. 3: 1.112-1.115.

Weiner, J. H., B. D. Lemire, M. L. Elmes, R. D. Bradley, and D. G. Scraba. 1984. Overproduction of fumarate reductase in *Escherichia coli* induces a novel intracellular lipid-protein organelle. J. Bacteriol. 158: 590-596.

Yano, T., C. Sanders, J. Catalana, and F. Daldal. 2005. sacB-5-Fluoroorotic Acid-pyrE-based bidirectional selection integration of unmarked alleles in the chromosome of *Rhodobacter capsulatus*. Appl. Environ. Microbiol. 71: 3014-3024.

I claim:

1. A method of expressing a polypeptide in a *Rhodospirillum* bacterium comprising growing the *Rhodospirillum* bacterium comprising a nucleic acid sequence encoding the polypeptide operably linked to a promoter selected from the group consisting of SEQ ID NO: 1 and a fragment of SEQ ID NO: 1 under conditions that allow expression of the polypeptide, wherein the *Rhodospirillum* bacterium is *Rhodospirillum rubrum* H2.

2. The method of claim 1, wherein the promoter comprises SEQ ID NO: 2.

3. The method of claim 1, further comprising isolating the polypeptide.

4. The method of claim 3, wherein the polypeptide is isolated by enriching for ICM.

5. The method of claim 1, wherein the polypeptide is a membrane polypeptide.

6. The method of claim 1, wherein the *Rhodospirillum* is grown under low oxygen tension.

7. The method of claim 1, wherein the *Rhodospirillum* is grown in the presence of an alternative electron acceptor.

8. The method of claim 7, wherein the alternative electron acceptor is selected from the group consisting of dimethyl sulfoxide, methionine sulfoxide, trimethylamine oxide and combinations thereof.

9. The method of claim 1, wherein the *Rhodospirillum* is grown to late log phase.

10. The method of claim 1, wherein the *Rhodospirillum* is grown semi-aerobically.

11. The method of claim 1, wherein the *Rhodospirillum* has reduced expression of a protein natively associated with the intracytoplasmic membrane as compared to the corresponding wild-type *Rhodospirillum*.

12. The method of claim 11, wherein the *Rhodospirillum* species has reduced expression of at least one of RC-H, RC-L, RC-M, LH-α, or LH-β.

13. The method of claim 11, wherein the *Rhodospirillum* species comprises a mutation in at least one of RC-H, RC-L, RC-M, LH-α, or LH-β.

14. The method of claim 1, wherein the nucleic acid sequence encoding the polypeptide is part of a vector.

15. A method of producing a *Rhodospirillum* bacterium capable of expressing a polypeptide comprising:
introducing a vector comprising a nucleic acid sequence encoding the polypeptide operably linked to a promoter selected from the group consisting of SEQ ID NO: 1 and a fragment of SEQ ID NO: 1 into the *Rhodospirillum* bacterium, wherein the *Rhodospirillum* bacterium is *Rhodospirillum rubrum* H2.

16. The method of claim 15, wherein the promoter comprises SEQ ID NO: 2.

17. The method of claim 15, wherein the polypeptide is a membrane polypeptide.

18. The method of claim 15, wherein the *Rhodospirillum* has reduced ability to express a protein natively associated with the intracytoplasmic membrane as compared to the corresponding wild-type *Rhodospirillum*.

19. A nucleic acid encoding a membrane polypeptide operably connected to a promoter selected from the group consisting of SEQ ID NO: 1 and a fragment of SEQ ID NO: 1, wherein the membrane polypeptide is not natively associated with the promoter.

20. The nucleic acid of claim 19, wherein the promoter comprises SEQ ID NO:2.

21. The nucleic acid of claim 19, further comprising a terminator fragment.

22. The nucleic acid of claim 19, wherein the nucleic acid further comprises a sequence encoding an affinity tag.

23. The nucleic acid of claim 19, further comprising a selectable or screenable marker for selection in a *Rhodospirillum*.

24. The nucleic acid of claim 19, wherein a vector comprises the nucleic acid.

25. A Rhodospirillum comprising the nucleic acid of claim 19, wherein the *Rhodospirillum* is *Rhodospirillum rubrum* H2.

26. A system for expressing a polypeptide in a *Rhodospirillum* comprising the *Rhodospirillum* and a vector comprising a promoter selected from the group consisting of SEQ ID NO: 1 and a fragment of SEQ ID NO: 1, wherein the *Rhodospirillum* bacterium is *Rhodospirillum rubrum* H2.

27. The system of claim 26, wherein the promoter comprises SEQ ID NO:2.

28. The system of claim 26, wherein the polypeptide is a membrane polypeptide.

29. The system of claim 26, wherein the *Rhodospirillum* has reduced ability to express a protein natively associated with the intracytoplasmic membrane as compared to the corresponding wild-type *Rhodospirillum*.

30. A Rhodospirillum bacterium comprising *Rhodospirillum rubrum* H2.

* * * * *

SEQUENCE LISTING

```
<160> NUMBER OF SEQ ID NOS: 30

<210> SEQ ID NO 1
<211> LENGTH: 1065
<212> TYPE: DNA
<213> ORGANISM: Rhodobacter capsulatus

<400> SEQUENCE: 1
cgacaggatc gtccttgccg cggcctccgg cgtgccggtc aggatctgcc ggatgaacag      60
cggcacgtcg atgtcggacg ggcaggccgt ggtgcagggc gcctcggcgc agaaatagca     120
gcgcgcggcg gccacctgcg cctgatgcgc cgtcaaaggc ggcgccacat cggcaaaggc     180
cgtgcaatac ccctcgggcg gaagacgccc ggggtgcacc ccgggtcgaa actggcttgt     240
ggtcactgtg acctccctgg ctttgttatt gccgcaaagg ctgccacgat ccgaaatttt     300
atcaataggt aaaatactga ggcgcaggga ttggcgcttc atggccgggc atctgcccaa     360
ggaatgggct gacgcagggg aaattgcgga aagagattcg ggacgaggcg caaaacggcg     420
gcgatgacca cggattcggc agggattcgg cagggattcg gcgcggctcg ggcccagaat     480
cacgcccggg cctgcgacaa tcacgtcaac gaagcgaagt gggaagccgt cagagcggtt     540
tcaagtgctt ccggcggata aattcggcgc gacaattcga cctgaaaatt ccggttgcct     600
```

```
gcgacaggcc gtccgggcgc gcgcgccgcc gccatcgccc gatctgcgac aggctaacgc    660
agtttaatgt acatcccgca tgacagtttg acccgaagcc cggttctggt cacgccgcaa    720
gccgcccgcc gcgcggggc cgcaaggcgc aaaccccctt tgcagcatgg ctcttgcgcc    780
```
*(Note: line 780 as printed)*

```
ctgtcgcacc ccccgccgca ggcgccgcgc cgcccgcgcc accggccccg gaatcgccca    840
aagatgcgtc tggaacacct gttttcactg ggattttgcg ccccggggg tggccgaatt    900 tgccgcagtg taagcccgac tttacacttg atcgccgaca cttgggctcc catagtgcgt    960
ctcacgaggt cggatcacag acggtccggc agcgggggg cgctgagacg gggctcgaac   1020
ttaaccgaga gagcttcatc aacgttccca atgatcccag ttttg                   1065

<210> SEQ ID NO 2
<211> LENGTH: 307
<212> TYPE: DNA
<213> ORGANISM: Rhodobacter capsulatus

<400> SEQUENCE: 2
tttgcagcat ggctcttgcg ccctgtcgca ccccccgccg caggcgccgc gccgcccgcg     60
ccaccggccc cggaatcgcc caaagatgcg tctggaacac ctgttttcac tgggattttg    120
cgcccccggg ggtggccgaa tttgccgcag tgtaagcccg actttacact tgatcgccga    180
cacttgggct cccatagtgc gtctcacgag gtcggatcac agacggtccg gcagcggggg    240
ggcgctgaga cggggctcga acttaaccga gagagcttca tcaacgttcc caatgatccc    300
agttttg                                                              307

<210> SEQ ID NO 3
<211> LENGTH: 27
<212> TYPE: DNA
<213> ORGANISM: Artificial Sequence
<220> FEATURE:
<223> OTHER INFORMATION: pucu1

<400> SEQUENCE: 3
ccctctagag cgacaggatc gtccttg                                         27

<210> SEQ ID NO 4
<211> LENGTH: 28
<212> TYPE: DNA
<213> ORGANISM: Artificial Sequence
<220> FEATURE:
<223> OTHER INFORMATION: pucu2

<400> SEQUENCE: 4
ccctctagat ttgcagcatg gctcttgc                                        28

<210> SEQ ID NO 5
<211> LENGTH: 27
<212> TYPE: DNA
<213> ORGANISM: Artificial Sequence
<220> FEATURE:
<223> OTHER INFORMATION: pucd

<400> SEQUENCE: 5
aaactcgagc aaaactggga tcattgg                                         27

<210> SEQ ID NO 6
<211> LENGTH: 26
<212> TYPE: DNA
<213> ORGANISM: Artificial Sequence
<220> FEATURE:
<223> OTHER INFORMATION: TF1
```

-continued

```
<400> SEQUENCE: 6
gtaattgggg catgccacat ggatga                                          26

<210> SEQ ID NO 7
<211> LENGTH: 27
<212> TYPE: DNA
<213> ORGANISM: Artificial Sequence
<220> FEATURE:
<223> OTHER INFORMATION: TR1

<400> SEQUENCE: 7
cggcggtcag aagcttgggc agcggat                                         27

<210> SEQ ID NO 8
<211> LENGTH: 45
<212> TYPE: DNA
<213> ORGANISM: Artificial Sequence
<220> FEATURE:
<223> OTHER INFORMATION: mscf

<400> SEQUENCE: 8
ggcaagaatt aggaggtagc acctatgggt cttctgagtg aattc                     45

<210> SEQ ID NO 9
<211> LENGTH: 42
<212> TYPE: DNA
<213> ORGANISM: Artificial Sequence
<220> FEATURE:
<223> OTHER INFORMATION: mscr

<400> SEQUENCE: 9
tcatcaatga tgatgatgat gatgcgactt gttctgctgg gc                        42

<210> SEQ ID NO 10
<211> LENGTH: 43
<212> TYPE: DNA
<213> ORGANISM: Artificial Sequence
<220> FEATURE:
<223> OTHER INFORMATION: msc1f2

<400> SEQUENCE: 10
gggcaagaat taggaggtag cacctatggg tcttctgagt gaa                       43

<210> SEQ ID NO 11
<211> LENGTH: 26
<212> TYPE: DNA
<213> ORGANISM: Artificial Sequence
<220> FEATURE:
<223> OTHER INFORMATION: P5

<400> SEQUENCE: 11
gagctcgccc ttcgccctgt tcgtcc                                          26

<210> SEQ ID NO 12
<211> LENGTH: 40
<212> TYPE: DNA
<213> ORGANISM: Artificial Sequence
<220> FEATURE:
<223> OTHER INFORMATION: P6

<400> SEQUENCE: 12
atacgacgtc atggaagtat gccgccaacg aggaaacgcc                           40

<210> SEQ ID NO 13
<211> LENGTH: 40
<212> TYPE: DNA
```

```
<213> ORGANISM: Artificial Sequence
<220> FEATURE:
<223> OTHER INFORMATION: P7

<400> SEQUENCE: 13
atacttccat gacgtcgtat ccttgccctc cgggtgtttc                              40

<210> SEQ ID NO 14
<211> LENGTH: 26
<212> TYPE: DNA
<213> ORGANISM: Artificial Sequence
<220> FEATURE:
<223> OTHER INFORMATION: P8

<400> SEQUENCE: 14
ctcgagtcgc cgccacgccg atccgc                                             26

<210> SEQ ID NO 15
<211> LENGTH: 43
<212> TYPE: DNA
<213> ORGANISM: Artificial Sequence
<220> FEATURE:
<223> OTHER INFORMATION: CytF

<400> SEQUENCE: 15
ggcaagaatt aggaggtagc acctatgagc tggaaaaaca ccg                          43

<210> SEQ ID NO 16
<211> LENGTH: 43
<212> TYPE: DNA
<213> ORGANISM: Artificial Sequence
<220> FEATURE:
<223> OTHER INFORMATION: CytR

<400> SEQUENCE: 16
tcatcaatga tgatgatgat gatggcgccg ttggggagc atc                           43

<210> SEQ ID NO 17
<211> LENGTH: 43
<212> TYPE: DNA
<213> ORGANISM: Artificial Sequence
<220> FEATURE:
<223> OTHER INFORMATION: phof

<400> SEQUENCE: 17
ggcaagaatt aggaggtagc acctatgcaa tccgtcgtga acc                          43

<210> SEQ ID NO 18
<211> LENGTH: 43
<212> TYPE: DNA
<213> ORGANISM: Artificial Sequence
<220> FEATURE:
<223> OTHER INFORMATION: phor

<400> SEQUENCE: 18
tcatcaatga tgatgatgat gatgcttcgg ggccttgcgc tcg                          43

<210> SEQ ID NO 19
<211> LENGTH: 67
<212> TYPE: DNA
<213> ORGANISM: Artificial Sequence
<220> FEATURE:
<223> OTHER INFORMATION: KcsF

<400> SEQUENCE: 19
ctcgagggca agaattagga ggtagcacct atgccgccca tgctgtccgg tcttctggcc        60
```

```
cgcttgg                                                              67

<210> SEQ ID NO 20
<211> LENGTH: 61
<212> TYPE: DNA
<213> ORGANISM: Artificial Sequence
<220> FEATURE:
<223> OTHER INFORMATION: KcsR

<400> SEQUENCE: 20
gggccctcat caatgatgat gatgatgatg atgccggcgg ttgtcgtcga gcatgcgctc    60
c                                                                    61

<210> SEQ ID NO 21
<211> LENGTH: 216
<212> TYPE: DNA
<213> ORGANISM: Rhodospirillum rubrum

<400> SEQUENCE: 21
gaatggcgct cggcgcttgg ggcgccgtgc aggccaccgc gaccggcgcg gccgttgccc    60
ttggcggcgg cttgcgcgat ggcgtttcct cgttggcggc atacttccat gacgtccctt   120
gccctccggg tgtttcacat tcggctgatc gcgctttatt tcgcgattct ggtggcgtgg   180
aacgtggcct cggctttgta tgacggccat ccgctg                             216

<210> SEQ ID NO 22
<211> LENGTH: 221
<212> TYPE: DNA
<213> ORGANISM: Rhodospirillum rubrum

<400> SEQUENCE: 22
cgcgacgccg ccgagcgcag cgcccgggcg gcgggtgaag acaggttac ggcggcgcgg     60 gttatccgcc tgctcgatct tcaggctgga gcgtaagggc gacttggagc acgacgctcc   120
ggcctgagct tgatcgcata gcctaccgtc cttgatcgcc tcgcggcgga acaggaccta   180
cggggcggga atggtcgaac agaccgttct cgccctgttg c                       221

<210> SEQ ID NO 23
<211> LENGTH: 1644
<212> TYPE: DNA
<213> ORGANISM: Homo sapiens

<400> SEQUENCE: 23
ctcgagggca agaattagga ggtagcacct atgtcgaaca agtgcgatgt ggtcgtggtc    60
ggcggcggca tctcgggcat ggccgccgcc aagctgctgc atgattcggg cctgaacgtc   120
gtcgtcctgg aggccgcgga tcacgtgggc ggccgcacct ataccctgcg caaccagaag   180
gtcaagtatg tcgatctggg cggcagctat gtcggcccca cccagaaccg catcctgcgc   240
ctggccaagg aactgggcct ggaaacctat aaggtgaacg aagtcgaacg cctgatccat   300
catgtcaagg gcaagtcgta tccgttccgc ggcccgttcc cgccggtgtg aaccccatc   360 acctatctgg accacaacaa cttctggcgc accatggacg atatgggccg cgagatccag   420
tcggacgccc cctggaaggc ccccctggcc gaagagtggg acaacatgac catgaaggaa   480
ctgctggaca gctgtgctg gaccgagagc gccaagcagc tggccaccct gttcgtgaac   540
ctgtgcgtga ccgccgaaac ccatgaggtg tcggccctgt ggttcctgtg gtatgtgaag   600
cagtgcggcg gcaccacccg catcatctcg accaccaacg gcggccagga acgcaagttc   660
gtgggcggca gcggccaggt ctcggagcgc atcatggacc tgctgggcga ccgcgtcaag   720
```

-continued

```
ctggagcgcc cggtcatcta tatcgatcag acccgcgaga acgtgctggt cgagaccctg      780
aaccatgaga tgtatgaggc caagtatgtc atcagcgcca tcccgcccac cctgggcatg      840
aagatccatt tcaaccccc cctgccgatg atgcgcaacc agatgatcac ccgcgtcccg       900
ctgggcagcg tcatcaagtg catcgtgtat tataaggaac cgttctggcg caagaaggat      960
tattgcggca ccatgatcat cgacggcgag aagccccgg tcgcctatac cctggacgat     1020
accaagccgg agggcaacta tgccgccatc atgggcttca tcctggccca taaggcccgc     1080
aagctggccc gcctgaccaa ggaagagcgc ctgaagaagc tgtgcgagct gtatgccaag     1140
gtgctgggct cgctggaggc cctggagccg gtgcattatg aggagaagaa ctggtgcgag     1200
gaacagtata gcggcggctg ctataccacc tatttcccgc cgggcatcct gacccagtat     1260
ggccgcgtcc tgcgccagcc ggtcgaccgc atctatttcg ccggcaccga aaccgccacc     1320
cactggtcgg gctatatgga gggcgccgtc gaggccggcg aacgcgccgc ccgcgaaatc     1380
ctgcatgcca tgggcaagat cccggaggac gagatctggc agtcggagcc cgagtcggtc     1440
gatgtcccgg cccagcccat caccaccacc ttcctggagc gccatctgcc ctcggtgccg     1500
ggcctgctgc cctgatcgg cctgaccacc atcttctcgg ccaccgccct gggcttcctg     1560
gcccataagc gcggcctgct ggtccgcgtg caccatcacc atcatcatga ttataaggat     1620
gacgatgata agtgatgagg gccc                                            1644
```

<210> SEQ ID NO 24
<211> LENGTH: 837
<212> TYPE: DNA
<213> ORGANISM: Homo sapiens

<400> SEQUENCE: 24

```
ctcgagggca agaattagga ggtagcacct atggaaggcg gcgccgccgc cgccaccccg       60
accgccctgc cgtattatgt cgccttctcg cagctgctgg gcctgaccct ggtcgccatg      120
accggcgcct ggctgggcct gtatcgcggc ggcatcgcct gggaatcgga tctgcagttc      180
aacgcccacc cgctgtgcat ggtgatcggc ctgatcttcc tgcagggcaa cgccctgctg      240
gtgtatcgcg tcttccgcaa cgaggccaag cgcaccacca aggtgctgca tggcctgctg      300
cacatcttcg ccctggtcat cgccctggtg ggcctggtcg ccgtcttcga ctatcatcgc      360
aagaagggct atgccgacct gtattcgctg cactcgtggt gcggcatcct ggtgttcgtg      420
ctgtatttcg tgcagtggct ggtgggcttc tcgttcttcc tgttcccggg cgcctcgttc      480
tcgctgcgct cgcgctatcg cccgcagcat atcttcttcg cgccaccat cttcctgctg      540
tcggtgggca ccgccctgct gggcctgaag aagccctgc tgttcaacct gggcggcaag      600
tattcggcct tcgagccgga gggcgtgctg gccaacgtcc tgggcctgct gctggcctgc     660
ttcggcggcg ccgtgctgta tcctgacc cgcgccgact ggaagcgccc ctcgcaggcc      720
gaggagcagg ccctgtcgat ggacttcaag accctgaccg aaggcgattc gccgggctcg     780
cagcatcacc accaccacca cgattataag gatgacgatg ataagtgatg agggccc         837
```

<210> SEQ ID NO 25
<211> LENGTH: 5680
<212> TYPE: DNA
<213> ORGANISM: Artificial Sequence
<220> FEATURE:
<223> OTHER INFORMATION: polynucleotide encoding human cytochrome b561
      (HCYC)

<400> SEQUENCE: 25

```
ctagatttgc agcatggctc ttgcgccctg tcgcaccccc gccgcaggcc cggcgccgcc       60
```

```
cgcgccaccg gccccggaat cgcccaaaga tgcgtctgga acacctgttt tcactgggat    120
tttgcgcccc cggggtggc cgaatttgcc gcagtgtaag cccgacttta cacttgatcg    180
ccgacacttg ggctcccata gtgcgtctca cgaggtcgga tcacagacgg tccggcagcg    240
ggggggcgct gagacgggc tcgaacttaa ccgagagagc ttcatcaacg ttcccaatga    300
tcccagtttt gctcgagggg gggcccgcca catggatgag tacgattccg aaccgatccg    360
tggactgcct gcggatctgc cgccgggcga attcatcctg tggcagggcg cgccgacacg    420
gcgcgccctt gccctccggg tgtttcacat tcggctgatc gcgctttatt tcgcgattct    480
ggtggcgtgg aacgtggcct cggctttgta tgacggccat ccgctgccca agctccagct    540
tttgttccct ttagtgaggg ttaattgcgc gcttggcgta atcatggtca tagctgtttc    600
ctgtgtgaaa ttgttatccg ctcacaattc cacacaacat acgagccgga agcataaagt    660
gtaaagcctg gggtgcctaa tgagtgagct aactcacatt aattgcgttg cgctcactgc    720
ccgctttcca gtcgggaaac ctgtcgtgcc agctgcatta atgaatcggc caacgcgcgg    780
ggagaggcgg tttgcgtatt gggcgcattt gcgcattcac agttctccgc aagaattgat    840
tggctccaat tcttggagtg tgaatccgt tagcgaggtg ccgccggctt ccattcaggt    900
cgaggtggcc cggctccatg caccgcgacg caacgcgggg aggcagacaa ggtatagggc    960
ggcgcctaca atccatgcca acccgttcca tgtgctcgcc gaggcggcat aaatcgccgt    1020
gacgatcagc ggtccagtga tcgaagttag gctggtaaga gccgcgagcg atccttgaag    1080
ctgtccctga tggtcgtcat ctacctgcct ggacagcatg gcctgcaacg cgggcatccc    1140
gatgccgccg gaagcgagaa gaatcataat ggggaaggcc atccagcctc gcgtcgcgaa    1200
cgccagcaag acgtagccca gcgcgtcggc cgccatgccg gcgataatgg cctgcttctc    1260
gccgaaacgt ttggtggcgg gaccagtgac gaaggcttga gcgagggcgt gcaagattcc    1320
gaataccgca agcgacaggc cgatcatcgt cgcgctccag cgaaagcggt cctcgccgaa    1380
aatgacccag agcgctgccg gcacctgtcc tacgagttgc atgataaaga agacagtcat    1440
aagtgcggcg acgatagtca tgccccgcgc ccaccggaag gagctgactg ggttgaaggc    1500
tctcaagggc atcggtcgac gctctcccct atgcgactcc tgcattagga agcagcccag    1560
tagtaggttg aggccgttga gcaccgccgc cgcaaggaat ggtgcatgca aggagatggc    1620
gcccaacagt cccccggcca cggggcctgc caccatacc cgccgaaac aagcgctcat    1680 gagcccgaag tggcgagccc gatcttcccc atcggtgatg tcggcgatat aggcgccagc    1740
aaccgcacct gtggcgccgg tgatgccggc cacgatgcgt ccggcgtaga ggatccacag    1800
gacgggtgtg gtcgccatga tcgcgtagtc gatagtggct ccaagtagcg aagcgagcag    1860
gactgggcgg cggccaaagc ggtcggacag tgctccgaga acgggtgcgc atagaaattg    1920
catcaacgca tatagcgcta gcagcacgcc atagtgactg gcgatgctgt cggaatggac    1980
gatatcccgc aagaggcccg gcagtaccgg cataaccaag cctatgccta cagcatccag    2040
ggtgacggtg ccgaggatga cgatgagcgc attgttagat tcatacacg gtgcctgact    2100 gcgttagcaa tttaactgtg ataaactacc gcattaaagc ttatcgatga taagctgtca    2160
aacatgagaa tcttgaaga cgaaagggcc tcgtgatacg cctattttta taggttaatg    2220
tcatgataat aatggtttct tagacgtcag gtggcacttt tcggggaaat gtgcgcgccc    2280
gcgttcctgc tggcgctggg cctgtttctg gcgctggact tccgctgtt ccgtcagcag    2340 cttttcgccc acgccttga tgatcgcggc ggccttggcc tgcatatccc gattcaacgg    2400
ccccagggcg tccagaacgg gcttcaggcg ctcccgaagg tctcgggccg tctcttgggc    2460
```

```
ttgatcggcc ttcttgcgca tctcacgcgc tcctgcggcg gcctgtaggg caggctcata    2520
cccctgccga accgcttttg tcagccggtc ggccacggct tccggcgtct caacgcgctt    2580
tgagattccc agcttttcgg ccaatccctg cggtgcatag gcgcgtggct cgaccgcttg    2640
cgggctgatg gtgacgtggc ccactggtgg ccgctccagg gcctcgtaga acgcctgaat    2700
gcgcgtgtga cgtgccttgc tgccctcgat gccccgttgc agcccagat cggccacagc    2760 ggccgcaaac gtggtctggt cgcgggtcat ctgcgctttg ttgccgatga actccttggc    2820
cgacagcctg ccgtcctgcg tcagcggcac acgaacgcg gtcatgtgcg ggctggtttc    2880
gtcacggtgg atgctggccg tcacgatgcg atccgccccg tacttgtccg ccagccactt    2940
gtgcgccttc tcgaagaacg ccgcctgctg ttcttggctg gccgacttcc accattccgg    3000
gctggccgtc atgacgtact cgaccgccaa cacagcgtcc ttgcgccgct tctctggcag    3060
caactcgcgc agtcgcccca tcgcttcatc ggtgctgctg gccgcccagt gctcgttctc    3120
tggcgtcctg ctggcgtcag cgttgggcgt ctcgcgctcg cggtaggcgt gcttgagact    3180
ggccgccacg ttgcccattt tcgccagctt cttgcatcgc atgatcgcgt atgccgccat    3240 gcctgccccct ccctttttggt gtccaaccgg ctcgacgggg gcagcgcaag gcggtgcctc    3300
cggcgggcca ctcaatgctt gagtatactc actagacttt gcttcgcaaa gtcgtgaccg    3360 cctacgcgg ctgcggcgcc ctacgggctt gctctccggg cttcgccctg cgcggtcgct    3420 gcgctcccctt gccagcccgt ggatatgtgg acgatggccg cgagcggcca ccggctggct    3480
cgcttcgctc ggcccgtgga caaccctgct ggacaagctg atggacaggc tgcgcctgcc    3540
cacgagcttg accacaggga ttgcccaccg gctacccagc cttcgaccac atacccaccg    3600
gctccaactg cgcggcctgc ggccttgccc catcaatttt tttaattttc tctggggaaa    3660
agcctccggc ctgcggcctg cgcgcttcgc ttgccggttg gacaccaagt ggaaggcggg    3720
tcaaggctcg cgcagcgacc gcgcagcggc ttggccttga cgcgcctgga acgacccaag    3780
cctatgcgag tgggggcagt cgaaggcgaa gcccgcccgc ctgccccccg agcctcacgg    3840
cggcgagtgc gggggttcca aggggggcagc gccaccttgg gcaaggccga aggccgcgca    3900
gtcgatcaac aagccccgga ggggccactt tttgccggag ggggagccgc gccgaaggcg    3960 tggggggaacc ccgcaggggt gcccttcttt gggcaccaaa gaactagata tagggcgaaa    4020
tgcgaaagac ttaaaaatca acaacttaaa aaagggggggt acgcaacagc tcattgcggc    4080
accccccgca atagctcatt gcgtaggtta agaaaatct gtaattgact gccacttta    4140 cgcaacgcat aattgttgtc gcgctgccga aaagttgcag ctgattgcgc atggtgccgc    4200
aaccgtgcgg caccctaccg catggagata agcatggcca cgcagtccag agaaatcggc    4260
attcaagcca agaacaagcc cggtcactgg gtgcaaacgg aacgcaaagc gcatgaggcg    4320
tgggccgggc ttattgcgag gaaacccacg gcggcaatgc tgctgcatca cctcgtggcg    4380
cagatgggcc accagaacgc cgtggtggtc agccagaaga cactttccaa gctcatcgga    4440
cgttctttgc ggacggtcca atacgcagtc aaggacttgg tggccgagcg ctggatctcc    4500
gtcgtgaagc tcaacggccc cggcaccgtg tcggcctacg tggtcaatga ccgcgtggcg    4560
tggggccagc cccgcgacca gttgcgcctg tcggtgttca gtgccgccgt ggtggttgat    4620
cacgacgacc aggacgaatc gctgttgggg catggcgacc tgcgccgcat cccgaccctg    4680
tatccgggcg agcagcaact accgaccggc cccggcgagg agccgccag ccagcccggc    4740 attccgggca tggaaccaga cctgccagcc ttgaccgaaa cggaggaatg gaacggcgc    4800 gggcagcagc gcctgccgat gcccgatgag ccgtgttttc tggacgatgg cgagccgttg    4860
```

```
gagccgccga cacgggtcac gctgccgcgc cggtagcact tgggttgcgc agcaacccgt    4920
aagtgcgctg ttccagacta tcggctgtag ccgcctcgcc gccctatacc ttgtctgcct    4980
ccccgcgttg cgtcgcggtg catggagccg ggccacctcg acctgaatgg aagccggcgg    5040
cacctcgcta acggattcac cgttttatc aggctctggg aggcagaata aatgatcata    5100
tcgtcaatta ttacctccac ggggagagcc tgagcaaact ggcctcaggc atttgagaag    5160
cacacggtca cactgcttcc ggtagtcaat aaaccggtaa accagcaata gacataagcg    5220
gctatttaac gaccctgccc tgaaccgacg accgggtcga atttgctttc gaatttctgc    5280
cattcatccg cttattatca cttattcagg cgtagcacca ggcgtttaag ggcaccaata    5340
actgccttaa aaaaattacg ccccgccctg ccactcatcg cagtcggcct attggttaaa    5400
aaatgagctg atttaacaaa aatttaacgc gaattttaac aaaatattaa cgcttacaat    5460
ttccattcgc cattcaggct gcgcaactgt tgggaagggc gatcggtgcg ggcctcttcg    5520
ctattacgcc agctggcgaa aggggatgt gctgcaaggc gattaagttg ggtaacgcca    5580
gggttttccc agtcacgacg ttgtaaaacg acggccagtg agcgcgcgta atacgactca    5640
ctatagggcg aattggagct ccaccgcggt ggcggccgct                          5680

<210> SEQ ID NO 26
<211> LENGTH: 570
<212> TYPE: DNA
<213> ORGANISM: Pseudomonas

<400> SEQUENCE: 26
atgagctgga aaacaccga atcccgttat gggagcctga ccattgccct gcactggctg     60
accctgctgc tgatcgccgg ggtctacgcc tgtatcgaac tgaagggcaa tttccccaag    120
ggcagcgaaa cccgcgaact gctcaagcaa tggcacttca tgcttggcct gagcgttttc    180
ctgctggtct ggttgcgcct gctggtgcgc ctggccaccc ctaccccgcg catagagccc    240
gccatccccg cctggcaggc gacgctggcc aggctgatgc actacgccct ctacctgatg    300
atgatcggcc tgcccttcgc cggctggctg atcctcagcg ccgccggcaa gccgataccg    360
ttcttcggcc tggagctacc gccgctggtc gacaagaacc ccgacctcgc cgggcaaatc    420
aaggaatggc acgaaaccat cggcaacgcc ggttatttcc tgatcggcct gcacgccgcc    480
gcggcgctct tccatcactt cgtcagccgc gacaacaccc tggtacggat gctcccccaa    540
cggcgccatc atcatcatca tcattgatga                                     570

<210> SEQ ID NO 27
<211> LENGTH: 1032
<212> TYPE: DNA
<213> ORGANISM: Homo sapiens

<400> SEQUENCE: 27
atgccgccct ccatctcagc tttccaggcc gcctacatcg gcatcgaggt gctcatcgcc     60
ctggtctctg tgcccgggaa cgtgctggtg atctgggcgg tgaaggtgaa ccaggcgctg    120
cgggatgcca ccttctgctt catcgtgtcg ctggcggtgg ctgatgtggc cgtgggtgcc    180
ctggtcatcc ccctcgccat cctcatcaac attgggccac agacctactt ccacacctgc    240
ctcatggttg cctgtccggt cctcatcctc acccagagct ccatcctggc cctgctggca    300
attgcggtgg accgctacct ccgggtcaag atccctctcc ggtacaagat ggtggtgacc    360
ccccggaggg cggcggtggc catagccggc tgctggatcc tctccttcgt ggtgggactg    420
accccctatg ttggctggaa caatctgagt gcggtggagc gggcctgggc agccaacggc    480
```

```
agcatggggg agcccgtgat caagtgcgag ttcgagaagg tcatcagcat ggagtacatg    540
gtctacttca acttctttgt gtgggtgctg ccccgcttc tcctcatggt cctcatctac    600
ctggaggtct tctacctaat ccgcaagcag ctcaacaaga aggtgtcgg ctcctccggc    660 gacccgcaga agtactatgg gaaggagctg aagatcgcca agtcgctggc cctcatcctc    720
ttcctctttg ccctcagctg gctgcctttg cacatcctca actgcatcac cctcttctgc    780
ccgtcctgcc acaagcccag catccttacc tacattgcca tcttcctcac gcacggcaac    840
tcggccatga accccattgt ctatgccttc cgcatccaga agttccgcgt caccttcctt    900
aagatttgga atgaccattt ccgctgccag cctgcacctc ccattgacga ggatctccca    960
gaagagaggc ctgatgacca tcatcatcat caccatggca ccgactataa ggacgatgat   1020
gataagtgat ga                                                       1032
```

<210> SEQ ID NO 28
<211> LENGTH: 57
<212> TYPE: DNA
<213> ORGANISM: Artificial Sequence
<220> FEATURE:
<223> OTHER INFORMATION: primer ADORA1Kpnpuf5

<400> SEQUENCE: 28

```
ggtaccggca agaattagga ggtagcacct atgccgccct ccatctcagc tttccag      57
```

<210> SEQ ID NO 29
<211> LENGTH: 80
<212> TYPE: DNA
<213> ORGANISM: Artificial Sequence
<220> FEATURE:
<223> OTHER INFORMATION: primer A1HFR

<400> SEQUENCE: 29

```
gcactgcagt catcactat catcatcgtc cttatagtcg gtgccatggt gatgatgatg    60
atggtcatca ggcctctctt                                               80
```

<210> SEQ ID NO 30
<211> LENGTH: 1353
<212> TYPE: DNA
<213> ORGANISM: Pseudomonas

<400> SEQUENCE: 30

```
atgcaatccg tcgtgaacca agactggcgt ggagcgctga tccgccacct gcttctcgtg    60
ctggctgcca gcctcgtgct cggcgtggtc agcggccatt acggctgggc cctggccctc   120
ggcctggctc tctacctcgg ctggacccct tggcagctac tgcgcctgca ccagtggctg   180
cgcaaccacc agccagacga gccaccgccg gacagctacg gcctctgggg cgaagtcttc   240
gacaatatct accacctgca acgccgcaac cagcgcgccc gtggccgcct gcaggcggtg   300
atcgaccgga tccaggagtc caccgcggcc ctgcgtgacg cggtgatcat gctcgacagc   360
gacggcaacc tggaatggtg gaacctcgcc gcggaaaacc tgctcggcct gaagaccccg   420
caggacggtg ccagccggt gagcaacctg atccgccatc gcgcgcttcaa ggaatacttc   480 gaccaggagg attaccgcga gccgctggaa atcccctcgc cgatcaacga gcgcctgcgc   540
ctgcaattcc acatcaccct ctacggcaac cgcgagcacc tgatgctggt ccgcgacgtc   600
acccgcgtcc accagctgga gcagatgcgc aaggatttcg tggccaacgt ctcccacgag   660
ctgcgcacgc cgctgacggt gatcgccggc tacctggaga ccctcctcga caacgtcgag   720
gatgtgaacc cgcgctggct gcgcgccctg cagcagatgc agcagcaggc cggacgcatg   780
```

-continued

```
cagaacctgc tcaacgacct gctcctgctg gccaagctgg aggccaccga ctaccccggc      840
gacaacaagc cggtggcggt ggacgctctc ctcgccagca tccgtaacga cgcccaggcc      900
ctgtccgccg ggcgcaacca ccgcatcagc ctggacgccg ccccgctgt gcagctcaag       960 ggcagcgagg cggaactgcg cagcgccttc tccaacctgg tattcaacgc ggtgaagtac     1020 accccgacg aaggcgagat ccgcatccgc tggtgggccg acgaacaggg cgcgcacctg     1080
tcggtgcagg acaccggtat cggcgtcgac cccaagcacc tgccgcgcct gaccgagcgc    1140
ttctaccggg tggactccag ccgcgcctcc aacaccggcg gcaccggcct cggcctggcc    1200
atcgtcaagc acgtgctgat ccgccaccgc gcgcgcctgg aaatcagcag cgtgcccggc    1260
aagggcagca ccttcacctg ccatttcgcc ccggcgcagg tcgccgaggc cgagcgcaag    1320
gccccgaagc atcatcatca tcatcattga tga                                 1353
```